(12) United States Patent
Kheir et al.

(10) Patent No.: US 10,357,450 B2
(45) Date of Patent: Jul. 23, 2019

(54) PROCESS FOR FORMING MICROBUBBLES WITH HIGH OXYGEN CONTENT AND USES THEREOF

(71) Applicant: Children's Medical Center Corporation, Boston, MA (US)

(72) Inventors: John Kheir, Boston, MA (US); Lindsay Thomson, Cambridge, MA (US); Andrew Loxley, Bethlehem, PA (US); Robert Lee, Bethlehem, PA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/390,665

(22) PCT Filed: Mar. 12, 2013

(86) PCT No.: PCT/US2013/030392
§ 371 (c)(1),
(2) Date: Oct. 3, 2014

(87) PCT Pub. No.: WO2013/151682
PCT Pub. Date: Oct. 10, 2013

(65) Prior Publication Data
US 2015/0164787 A1    Jun. 18, 2015

Related U.S. Application Data

(60) Provisional application No. 61/261,261, filed on Apr. 6, 2012.

(51) Int. Cl.
| | | |
|---|---|---|
| *A61K 9/00* | (2006.01) | |
| *A61K 33/00* | (2006.01) | |
| *B01F 7/00* | (2006.01) | |
| *B01F 3/04* | (2006.01) | |
| *B01F 3/08* | (2006.01) | |

(52) U.S. Cl.
CPC ............ *A61K 9/0026* (2013.01); *A61K 33/00* (2013.01); *B01F 3/04453* (2013.01); *B01F 3/0807* (2013.01); *B01F 7/00758* (2013.01)

(58) Field of Classification Search
None
See application file for complete search history.

(56) References Cited

U.S. PATENT DOCUMENTS

| | | | |
|---|---|---|---|
| 3,526,481 A | 9/1970 | Rubricius et al. | |
| 4,276,885 A | 7/1981 | Tickner et al. | |
| 4,446,642 A | 5/1984 | Chap | |
| 4,466,442 A | 8/1984 | Hilmann et al. | |
| 4,844,882 A | 7/1989 | Widder et al. | |
| 4,911,689 A | 3/1990 | Hattler | |
| 5,084,011 A | 1/1992 | Grady | |
| 5,219,538 A | 6/1993 | Henderson et al. | |
| 5,487,390 A | 1/1996 | Cohen et al. | |
| 5,558,094 A | 9/1996 | Quay | |
| 5,573,751 A | 11/1996 | Quay | |
| 5,665,383 A | 9/1997 | Grinstaff et al. | |
| 5,711,933 A | 1/1998 | Bichon et al. | |
| 5,827,504 A * | 10/1998 | Yan ..................... A61K 49/223 424/9.52 |
| 5,840,275 A | 11/1998 | Bichon et al. | |
| 5,863,520 A | 1/1999 | Bichon et al. | |
| 5,869,538 A | 2/1999 | Van Liew et al. | |
| 5,882,717 A * | 3/1999 | Panesar ..................... A23F 5/40 426/443 |
| 5,935,553 A | 8/1999 | Unger et al. | |
| 6,045,777 A | 4/2000 | Church et al. | |
| 6,200,548 B1 | 3/2001 | Bichon et al. | |
| 6,210,611 B1 | 4/2001 | Needham et al. | |
| 6,261,537 B1 | 7/2001 | Klaveness et al. | |

(Continued)

FOREIGN PATENT DOCUMENTS

| | | |
|---|---|---|
| EP | 0077752 A2 | 4/1983 |
| EP | 0699445 A2 | 3/1996 |

(Continued)

OTHER PUBLICATIONS

International Search Report and Written Opinion for PCT/US2013/030392 dated Aug. 14, 2013.
International Preliminary Report on Patentability for PCT/US2013/030392 dated Oct. 16, 2014.
[No Author Listed], Acute Myocardial Infarction with HyperOxemic Therapy II (Amihot II). Clinical Trials.gov. Last Accessed from http://clinicaltrials.gov/ct2/show/NCT00175058?tern=therox &rank=1 on Nov. 9, 2010. 5 pages.
[No Author Listed], DownStream System. Therox. Last Accessed from http://www.therox.com/products/downstream-system/index.cfm?print on Nov. 9, 2010. 1 page.
Adjei et al., Pulmonary delivery of peptide drugs: effect of particle size on bioavailability of leuprolide acetate in healthy male volunteers. Pharm Res. Jun. 1990;7(6):565-9.

(Continued)

*Primary Examiner* — Robert A Wax
*Assistant Examiner* — Danah Al-Awadi
(74) *Attorney, Agent, or Firm* — Wolf, Greenfield & Sacks, P.C.

(57) ABSTRACT

Formulations containing a carrier and microbubbles encapsulating oxygen gas, and methods for making and using the formulations are described herein. The formulations are manufactured by a process which includes high shear homogenization. The resulting microbubble suspension may be centrifuged to further concentrate the microbubbles. The resulting concentrated LOM suspension preferably has an oxygen content ranging from 50 to 99% (vol). Prior to administration to a patient, the viscosity of the LOM suspension may be reduced to the desired viscosity, preferably similar to the viscosity of the patient's blood. The resulting LOM formulation typically has an oxygen concentration ranging from 65 to 80% (vol). The microbubbles are formed from one or more lipids, preferably one or more phospholipids, most preferably DSPC, and preferably also contain one or more stabilizing agents/excipients, preferably cholesterol.

14 Claims, 17 Drawing Sheets

(56) References Cited

U.S. PATENT DOCUMENTS

| | | | |
|---|---|---|---|
| 6,315,981 | B1 | 11/2001 | Unger |
| 6,333,021 | B1 | 12/2001 | Schneider et al. |
| 6,416,740 | B1 | 7/2002 | Unger |
| 6,443,898 | B1 | 9/2002 | Unger et al. |
| 6,537,246 | B1* | 3/2003 | Unger ................. A61K 49/223 222/145.5 |
| 6,808,720 | B2 | 10/2004 | Unger |
| 6,844,317 | B2 | 1/2005 | Winslow et al. |
| 7,105,151 | B2 | 9/2006 | Unger et al. |
| 7,122,027 | B2 | 10/2006 | Trescony et al. |
| 7,141,235 | B2 | 11/2006 | Trevino et al. |
| 7,303,156 | B1 | 12/2007 | Kim et al. |
| 8,481,077 | B2 | 7/2013 | Kheir et al. |
| 2002/0155098 | A1 | 10/2002 | Bolton |
| 2003/0120204 | A1 | 6/2003 | Unger et al. |
| 2004/0013662 | A1 | 1/2004 | Porter et al. |
| 2005/0260189 | A1 | 11/2005 | Klibanov et al. |
| 2006/0051297 | A1 | 3/2006 | Schneider et al. |
| 2007/0134332 | A1 | 6/2007 | Turnell et al. |
| 2009/0191244 | A1* | 7/2009 | Kheir ............... A61K 47/48869 424/400 |
| 2010/0069814 | A1 | 3/2010 | Borgia et al. |
| 2010/0080759 | A1 | 4/2010 | Chang et al. |
| 2010/0158813 | A1 | 6/2010 | Paradossi et al. |
| 2010/0209532 | A1 | 8/2010 | Dube et al. |
| 2011/0207062 | A1 | 8/2011 | McAlister |
| 2012/0156300 | A1 | 6/2012 | Kheir et al. |
| 2012/0175305 | A1 | 7/2012 | Borden et al. |
| 2012/0201900 | A1 | 8/2012 | Borden et al. |
| 2013/0066264 | A1 | 3/2013 | Matsumoto et al. |
| 2014/0010848 | A1 | 1/2014 | Kheir et al. |
| 2014/0057108 | A1 | 2/2014 | Sun et al. |
| 2016/0030596 | A1 | 2/2016 | Kheir et al. |
| 2016/0067276 | A1 | 3/2016 | Polizzotti et al. |

FOREIGN PATENT DOCUMENTS

| | | |
|---|---|---|
| EP | 0 605 477 B2 | 6/2007 |
| EP | 2253308 A1 | 11/2010 |
| WO | WO 98/18501 A2 | 5/1988 |
| WO | WO 92/05806 A1 | 4/1992 |
| WO | WO 92/17514 A1 | 10/1992 |
| WO | WO 94/18954 A1 | 9/1994 |
| WO | WO 94/28874 A1 | 12/1994 |
| WO | WO 95/16467 A1 | 6/1995 |
| WO | WO 97/00638 A1 | 1/1997 |
| WO | WO 97/22409 A1 | 6/1997 |
| WO | WO 2004/069284 * | 8/2004 |
| WO | WO 2004/069284 A2 | 8/2004 |
| WO | WO 2005/063305 A1 | 7/2005 |
| WO | WO 2009/043031 A2 | 4/2009 |
| WO | WO 2009/082449 A2 | 7/2009 |
| WO | WO 2011/013032 A2 | 2/2011 |
| WO | WO 2011/034892 A2 | 3/2011 |
| WO | WO 2012/065060 A2 | 5/2012 |
| WO | WO 2015/196065 A1 | 12/2015 |

OTHER PUBLICATIONS

Asai et al., Interaction of soybean oil with phosphatidylcholine and their formation of small dispersed particles. Drug Dev Ind Pharm. May 1999;25(5):643-50.

Baker et al., Hypothermia prevents ischemia-induced increases in hippocampal glycine concentrations in rabbits. Stroke. May 1991;22(5):666-73.

Barnhart et al., Characteristics of Albunex: air-filled albumin microspheres for echocardiography contrast enhancement. Invest Radiol. Sep. 1990;25 Suppl 1:S162-4.

Batchelor et al., The determination of the bulk stress in a suspension of spherical particles to order c2. J Fluid Mech. 1972;56(3):401-27.

Bisazza et al., Microbubble-mediated oxygen delivery to hypoxic tissues as a new therapeutic device. Conf Proc IEEE Eng Med Biol Soc. 2008;2008:2067-70.

Borden et al., Oxygen permeability of fully condensed lipid monolayers. J Phys Chem. 2004;108(19):6009-16.

Borden et al., a stimulus-responsive contrast agent for ultrasound molecular imaging. Biomaterials. Feb. 2008;29(5):597-606. Epub Oct. 30, 2007.

Borden et al., Dissolution behavior of lipid monolayer-coated, air filled microbubbles: Effect of lipid hydrophobic chain length. Langmuir. 2002;18(24):9225-33.

Borden et al., Influence of lipid shell physicochemical properties on ultrasound-induced microbubble destruction. IEEE Trans Ultrason Ferroelectr Freq Control. Nov. 2005;52(11):1992-2002.

Borden et al., Lateral phase separation in lipid-coated microbubbles. Lateral phase separation in lipid-coated microbubbles. Langmuir. Apr. 25, 2006;22(9):4291-7.

Borden et al., Physico-chemical properties of the microbubble lipid shell. IEEE Transactions on Ultrasonics Ferroelectrics and Frequency Control, Montreal, Canada (2004).

Borden et al., Surface phase behavior and microstructure of lipid/PEG-emulsifier monolayer-coated microbubbles. Colloids Surf B Biointerfaces. Jun. 1, 2004;35(3-4):209-23.

Brancewicz et al., Hydrophobic gas bubble formation in definity (R): a freeze fracture electron microscopy study. J Dispersion Sci Tech. 2006;27(5):761-5.

Brezis et al., Hypoxia of the renal medulla—its implications for disease. N Engl J Med. Mar. 9, 1995;332(10):647-55.

Bucana et al., Preservation of multilamellar lipid vesicles (liposomes) for ultrastructural studies. Scan Electron Microsc. 1983;(Pt 3):1329-37.

Burkhard et al., Oxygen transport to tissue by persistent bubbles: theory and simulations. J Appl Physiol. 1994;77(6):2874-8.

Cabrales et al., Early difference in tissue pH and microvascular hemodynamics in hemorrhagic shock resuscitation using polyethylene glycol-albumin- and hydroxyethyl starch-based plasma expanders. Shock. Jul. 2005;24(1):66-73.

Cabrales et al., Extreme hemodilution with PEG-hemoglobin vs. PEG-albumin. Am J Physiol Heart Circ Physiol. Dec. 2005;289(6):H2392-400. Epub Jul. 15, 2005.

Choi et al., Liposomes and niosomes as topical drug delivery systems. Skin Pharmacol Physiol. Sep.-Oct. 2005;18(5):209-19. Epub Jul. 5, 2005.

Choi et al., Noninvasive, transcranial and localized opening of the blood-brain barrier using focused ultrasound in mice. Ultrasound Med Biol. Jan. 2007;33(1):95-104.

Cortesi et al., Sugar cross-linked gelatin for controlled release: microspheres and disks. Biomaterials. Sep. 1998;19(18):1641-9.

Dewall et al., A simple, expendable, artificial oxygenator for open heart surgery. Surg Clin North Am. Aug. 1956:1025-34.

Diebel et al., Right ventricular response after myocardial contusion and hemorrhagic shock. Surgery. Oct. 1993;114(4):788-92; discussion 793.

Dressaire et al., Interfacial polygonal nanopatterning of stable microbubbles. Science. May 30, 2008;320(5880):1198-201.

Dubourg et al., Failure of the loop diuretic torasemide to improve renal function of hypoxemic vasomotor nephropathy in the newborn rabbit. Pediatr Res. Apr. 2000;47(4 Pt 1):504-8.

Duncan et al., Test of the Epstein-Plesset model for gas microparticle dissolution in aqueous media: effect of surface tension and gas undersaturation in solution. Langmuir. Mar. 30, 2004;20(7):2567-78.

Elberger et al., Double-labeling of tissue containing the carbocyanine dye DiI for immunocytochemistry. J Histochem Cytochem. May 1990;38(5):735-9.

El-Desoky et al., Effect of graded hypoxia on hepatic tissue oxygenation measured by near infrared spectroscopy. J Hepatol. Jul. 1999;31(1):71-6.

Epstein et al., On the stability of gas bubbles in liquid-gas solutions. J Chem Phys. 1950;18(11):1505-9.

Farook et al., Microbubbling by co-axial electrohydrodynamic atomization. Med Biol Eng Comput. Aug. 2007;45(8):781-9. Epub Jul. 12, 2007.

Farook et al., Preparation of microbubble suspensions by co-axial electrohydrodynamic atomization. Med Eng Phys. Sep. 2007;29(7):749-54. Epub Oct. 10, 2006.

(56) References Cited

OTHER PUBLICATIONS

Feinstein et al., Microbubble dynamics visualized in the intact capillary circulation. J Am Coll Cardiol. Sep. 1984;4(3):595-600.
Feinstein, The powerful microbubble: from bench to bedside, from intravascular indicator to therapeutic delivery system, and beyond. Am J Physiol Heart Circ Physiol. Aug. 2004;287(2):H450-7.
Ferrara et al., Ultrasound microbubble contrast agents: fundamentals and application to gene and drug delivery. Annu Rev Biomed Eng. 2007;9:415-47.
Feshitan et al., Microbubble size isolation by differential centrifugation. J Colloid Interface Sci. Jan. 15, 2009;329(2):316-24. doi: 10.1016/j.jcis.2008.09.066. Epub Oct. 1, 2008.
Fuchs et al., Ischemic hepatitis: clinical and laboratory observations of 34 patients. J Clin Gastroenterol. Apr. 1998;26(3):183-6.
Gerber et al., Long lived microbubbles for oxygen delivery. Artif Cells Blood Substit Immobil Biotechnol. 2007;35(1):119-24.
Hansel et al., Metabolic syndrome is associated with elevated oxidative stress and dysfunctional dense high-density lipoprotein particles displaying impaired antioxidative activity. J Clin Endocrinol Metab. Oct. 2004;89(10):4963-71.
Hattler et al., A respiratory gas exchange catheter: in vitro and in vivo tests in large animals. J Thorac Cardiovasc Surg. Sep. 2002;124(3):520-30.
Hernot et al., Microbubbles in ultrasound-triggered drug and gene delivery. Adv Drug Deliv Rev. Jun. 30, 2008;60(10):1153-66. Epub Apr. 3, 2008.
Jones et al., Demonstration of nonperfused myocardium in late hemorrhagic shock. Circ Shock. 1978;5(2):97-104.
Karlsson et al., Dynamics of hepatic enzyme activity following birth asphyxia. Acta Paediatr. Nov. 2006;95(11):1405-11.
Kaya et al., Changes in lipid-encapsulated microbubble population during continuous infusion and methods to maintain consistency. Ultrasound Med Biol. Oct. 2009;35(10):1748-55. doi: 10.1016/j.ultrasmedbio.2009.04.023. Epub Jul. 26, 2009.
Kheir et al., Bulk manufacture of concentrated oxygen gas-filled microparticles for intravenous oxygen delivery. Adv Healthc Mater. Aug. 2013;2(8):1131-41. doi: 10.1002/adhm.201200350. Epub Mar. 8, 2013.
Kheir et al., Novel oxygen-bearing nanoparticles provide dose-dependent oxygen delivery. Critic Care Medic. 2007;35(12):A16-16.
Kim et al., Artificial oxygen carriers as red blood cell substitutes: a selected review and current status. Artif Organs. Sep. 2004;28(9):813-28.
Kim et al., Mechanical properties and microstructure of polycrystalline phospholipid monolayer shells: novel solid microparticles. Langmuir. 2003;19(20):8455-66.
Kim et al., New protocols for preparing dipalmitoylphosphatidylcholine dispersions and controlling surface tension and competitive adsorption with albumin at the air/aqueous interface. Colloids Surf B Biointerfaces. Jul. 10, 2005;43(3-4):256-66.
Kim, Mechanical properties, microstructure, and specific adhesion of phospholipid monolayer-coated microbubbles. Ph.D. Dissertation, Duke University, (1999).
Klemcke et al., Is survival time after hemorrhage a heritable, quantitative trait?: an initial assessment. Shock. Jun. 2008;29(6):748-53.
Klibanov et al., Amphipathic polyethyleneglycols effectively prolong the circulation time of liposomes. FEBS Lett. Jul. 30, 1990;268(1):235-7.
Klibanov et al., Ultrasound contrast agents: development of the field and current status. Topics Curr Chem. 2002;222:1-34.
Kohane et al., A re-examination of tetrodotoxin for prolonged duration local anesthesia. Anesthesiology. Jul. 1998;89(1):119-31.
Kohane et al., Sciatic nerve blockade in infant, adolescent, and adult rats: a comparison of ropivacaine with bupivacaine. Anesthesiology. Nov. 1998;89(5):1199-208; discussion 10A.
Kuhl et al., Modulation of interaction forces between bilayers exposing short-chained ethylene oxide headgroups. Biophys J. May 1994;66(5):1479-88.
Kvale et al., Size fractionation of gas-filled microspheres by flotation. Separations Technol. 1996;6(4):219-26.
Laine et al., Polyethylene glycol nephrotoxicity secondary to prolonged high-dose intravenous lorazepam. Ann Pharmacother. Nov. 1995;29(11):1110-4.
Ledingham, Heart failure in experimental refractory shock. Eur J Intensive Care Med. Nov. 1976;2(3):111-7.
Leonov et al., Extending the golden hour of hemorrhagic shock tolerance with oxygen plus hypothermia in awake rats. An exploratory study. Resuscitation. Feb. 2002;52(2):193-202.
Li et al., Acoustic emulsification Part 1. Instability of oil-water interface to form initial droplets. J Fluid Mech. 1978;88(Oct):499-511.
Li et al., Acoustic Emulsification Part 2. Breakup of large primary oil droplets in a water medium. J Fluid Mech. 1978;88(Oct):513-28.
Lindner, Microbubbles in medical imaging: current applications and future directions. Nat Rev Drug Discov. Jun. 2004;3(6):527-32.
Lum et al., Ultrasound radiation force enables targeted deposition of model drug carriers loaded on microbubbles. J Control Release. Mar. 10, 2006;111(1-2):128-34. Epub Dec. 27, 2005.
Lundgren et al., Intravascular fluorocarbon-stabilized microbubbles protect against fatal anemia in rats. Artif Cells Blood Substit Immobil Biotechnol. 2006;34(5):473-86.
Masters et al., Prolonged regional nerve blockade by controlled release of local anesthetic from a biodegradable polymer matrix. Anesthesiology. Aug. 1993;79(2):340-6.
McLure et al., Review of local anaesthetic agents. Minerva Anestesiol. Mar. 2005;71(3):59-74.
Meade et al., Ventilation strategy using low tidal volumes, recruitment maneuvers, and high positive end-expiratory pressure for acute lung injury and acute respiratory distress syndrome: a randomized controlled trial. JAMA. Feb. 13, 2008;299(6):637-45.
Meure et al., Conventional and dense gas techniques for the production of liposomes: a review. AAPS PharmSciTech. 2008;9(3):798-809. doi: 10.1208/s12249-008-9097-x. Epub Jul. 3, 2008.
Mezzetti et al., Oxidative stress and cardiovascular complications in diabetes: isoprostanes as new markers on an old paradigm. Cardiovasc Res. Aug. 18, 2000;47(3):475-88.
Mulholland et al., Investigation and quantification of the blood trauma caused by the combined dynamic forces experienced during cardiopulmonary bypass. Perfusion. Nov. 2000;15(6):485-94.
O'Neill et al., Acute Myocardial Infarction with Hyperoxemic Therapy (AMIHOT): a prospective, randomized trial of intracoronary hyperoxemic reperfusion after percutaneous coronary intervention. J Am Coll Cardiol. Jul. 31, 2007;50(5):397-405. Epub Jul. 16, 2007.
Pancholi et al., Generation of microbubbles for diagnostic and therapeutic applications using a novel device. J Drug Target. Jul. 2008;16(6):494-501. doi: 10.1080/10611860802184884.
Pancholi et al., Novel methods for preparing phospholipid coated microbubbles. Eur Biophys J. Apr. 2008;37(4):515-20. Epub Aug. 9, 2007.
Pu et al., Collapse and shedding transitions in binary lipid monolayers coating microbubbles. Langmuir. Mar. 28, 2006;22(7):2993-9.
Pu et al., Effect of microstructure on molecular oxygen permeation through condensed phospholipid monolayers. J Am Chem Soc. May 11, 2005;127(18):6524-5.
Ryter et al., Heme oxygenase-1/carbon monoxide: from basic science to therapeutic applications. Physiol Rev. Apr. 2006;86(2):583-650.
Sakai et al., Hemoglobin-vesicles as oxygen carriers: influence on phagocytic activity and histopathological changes in reticuloendothelial system. Am J Pathol. Sep. 2001;159(3):1079-88.
Scholz, Mechanisms of (local) anaesthetics on voltage-gated sodium and other ion channels. Br J Anaesth. Jul. 2002;89(1):52-61.
Schubert et al., Using microbubbles to oxygenate blood: possible? Engineering in Medicine and Biology Society, 2003. Proceedings of the 25 Annual International Conference of the IEEE, 1(17-21):431-34 (2003).
Stieger et al., Enhancement of vascular permeability with low-frequency contrast-enhanced ultrasound in the chorioallantoic membrane model. Radiology. Apr. 2007;243(1):112-21.
Suslick et al., Acoustic Cavitation and Its Chemical Consequences. Phil. Trans. Roy. Soc. A. 1999;357:335-353.

(56) References Cited

OTHER PUBLICATIONS

Swanson et al., Phospholipid-stabilized microbubble foam for injectable oxygen delivery. Langmuir. Oct. 19, 2010;26(20):15726-9. doi: 10.1021/la1029432.
Takalkar et al., Binding and detachment dynamics of microbubbles targeted to P-selectin under controlled shear flow. J Control Release. May 18, 2004;96(3):473-82.
Takasu et al., Effects of increased oxygen breathing in a volume controlled hemorrhagic shock outcome model in rats. Resuscitation. Aug. 1, 2000;45(3):209-20.
Talu et al., Lipid-stabilized monodispersed microbubbles produced by flow focusing for use as ultrasound contrast agents. Ultrasonics Symposium, 2006 IEEE. 2006;2-6:1568-71.
Talu et al., Long-term stability by lipid coating monodisperse microbubbles formed by a flow-focusing device. Langmuir. Nov. 7, 2006;22(23):9487-90.
Talu et al., Maintaining monodispersity in a microbubble population formed by flow-focusing. Langmuir. Mar. 4, 2008;24(5):1745-9. Epub Jan. 19, 2008.
Talu et al., Tailoring the size distribution of ultrasound contrast agents: possible method for improving sensitivity in molecular imaging. Mol Imaging. Nov.-Dec. 2007;6(6):384-92.
Tayar et al., Severe hyperosmolar metabolic acidosis due to a large dose of intravenous lorazepam. N Engl J Med. Apr. 18, 2002;346(16):1253-4.
Taylor, Ostwald ripening in emulsions. Advances in Colloid and Interface Science. 1998;75(2):107-63.
Tracy et al., A method to fix lipids for staining fat embolism in paraffin sections. Histopathology. Jul. 2002;41(1):75-9.
Unger et al., Acoustically active liposheres containing paclitaxel: a new therapeutic ultrasound contrast agent. Invest Radiol. Dec. 1998;33(12):886-92.
Unger et al., Therapeutic applications of lipid-coated microbubbles. Adv Drug Deliv Rev. May 7, 2004;56(9):1291-314.
Vercherat et al., Stra13 regulates oxidative stress mediated skeletal muscle degeneration. Hum Mol Genet. Nov. 15, 2009;18(22):4304-16. doi: 10.1093/hmg/ddp383. Epub Aug. 13, 2009.
Wheatley et al., Surfactant-stabilized contrast agent on the nanoscale for diagnostic ultrasound imaging. Ultrasound Med Biol. Jan. 2006;32(1):83-93.
Winslow et al., Comparison of PEG-modified albumin and hemoglobin in extreme hemodilution in the rat. J Appl Physiol. Oct. 2004;97(4):1527-34. Epub Jun. 18, 2004.
Wu et al., Ultrasound, cavitation bubbles and their interaction with cells. Adv Drug Deliv Rev. Jun. 30, 2008;60(10):1103-16. Epub Apr. 8, 2008.
Xu et al., Controllable gas-liquid phase flow patterns and monodisperse microbubbles in a microfluidic T-junction device. Applied Physics Letters. 2006;88(13).
Zanen et al., The optimal particle size for parasympathicolytic aerols in mild asthmatics. Int J Pharm. 1995;114:111-5.
Davis et al., Topical oxygen emulsion: a novel wound therapy. Arch Dermatol. Oct. 2007;143(10):1252-6.
Silvay et al., Cardiopulmonary bypass for adult patients: a survey of equipment and techniques. J Cardiothorac Vasc Anesth. Aug. 1995;9(4):420-4.
Sirsi et al., Microbubble Compositions, Properties and Biomedical Applications. Bubble Sci Eng Technol. Nov. 2009;1(1-2):3-17.
Sevitt, A review of the complications of burns, their origin and importance for illness and death. J Trauma. May 1979;19(5):358-69. Abstract Only.
Xiong et al., Polymeric microbubbles for ultrasonic molecular imaging and targeted therapeutics. J Biomater Sci Polym Ed. 2011;22(4-6):417-28. doi: 10.1163/092050610X540440.
European Office Action dated Dec. 5, 2018 for Application No. EP 11840660.2.

Invitation to Pay Additional Fees dated Apr. 23, 2018 for Application No. PCT/US2018/020305.
International Search Report and Written Opinion dated Jun. 25, 2018 for Application No. PCT/US2018/020305.
Bauer et al., Perfluorocarbon-filled poly(lactide-co-gylcolide) nano- and microcapsules as artificial oxygen carriers for blood substitutes: a physico-chemical assessment. J Microencapsul. 2010;27(2):122-32. doi: 10.3109/02652040903052002.
Cravotto et al., On the mechanochemical activation by ultrasound. Chem Soc Rev. Sep. 21, 2013;42(18):7521-34. doi: 10.1039/c2cs35456j.
De Jong et al., Basic acoustic properties of microbubbles. Echocardiography. Apr. 2002;19(3):229-40.
Ferenz et al., Safety of poly (ethylene glycol)-coated perfluorodecalin-filled poly (lactide-co-glycolide) microcapsules following intravenous administration of high amounts in rats. Results Pharma Sci. Apr. 30, 2014;4:8-18. doi: 10.1016/j.rinphs.2014.04.001. eCollection 2014.
Feshitan et al., Systemic oxygen delivery by peritoneal perfusion of oxygen microbubbles. Biomaterials. Mar. 2014;35(9):2600-6. doi: 10.1016/j.biomaterials.2013.12.070. Epub Jan. 15, 2014.
Kheir et al., Oxygen gas-filled microparticles provide intravenous oxygen delivery. Sci Transl Med. Jun. 27, 2012;4(140):140ra88. doi: 10.1126/scitranslmed.3003679.
Kutscher et al., Threshold size for optimal passive pulmonary targeting and retention of rigid microparticles in rats. J Control Release. Apr. 2, 2010;143(1):31-7. doi: 10.1016/j jconrel.2009.12.019. Epub Jan. 5, 2010.
Paefgen et al., Evolution of contrast agents for ultrasound imaging and ultrasound-mediated drug delivery. Front Pharmacol. Sep. 15, 2015;6:197. doi: 10.3389/fphar.2015.00197. eCollection 2015.
Peng et al., Interfacial Nanoprecipitation toward Stable and Responsive Microbubbles and Their Use as a Resuscitative Fluid. Angew Chem Int Ed Engl. Jan. 26, 2018;57(5):1271-1276. doi: 10.1002/anie.201711839. Epub Jan. 2, 2018.
Rodriguez et al., Generation of microbubbles with applications to industry and medicine. Annu. Rev. Fluid Mech. 47, 405-429 (2015).
Seekell et al., Oxygen delivery using engineered microparticles. Proc Natl Acad Sci U S A. Nov. 1, 2016;113(44):12380-12385. Epub Oct. 17, 2016.
Span et al., Engineered microparticles delivering oxygen to enhance radiotherapy efficacy. Proc Natl Acad Sci U S A. Dec. 13, 2016;113(50):E8009. Epub Dec. 7, 2016.
Spiess, Perfluorocarbon emulsions as a promising technology: a review of tissue and vascular gas dynamics. J Appl Physiol (1985). Apr. 2009;106(4):1444-52. doi: 10.1152/japplphysiol.90995.2008. Epub Jan. 29, 2009.
Teraphongphom et al., Nanoparticle Loaded Polymeric Microbubbles as Contrast Agents for Multimodal Imaging. Langmuir. Nov. 3, 2015;31(43):11858-67. doi: 10.1021/acs.langmuir.5b03473. Epub Oct. 16, 2015.
Tsao et al., Enzyme-Degradable Hybrid Polymer/Silica Microbubbles as Ultrasound Contrast Agents. Langmuir. Jun. 28, 2016;32(25):6534-43. doi: 10.1021/acs.langmuir.6b01075. Epub Jun. 16, 2016.
Zhao et al., Preparation, characterization and in vivo observation of phospholipid-based gas-filled microbubbles containing hirudin. Ultrasound Med Biol. Sep. 2005;31(9):1237-43.
Zhao et al., Radiation-force assisted targeting facilitates ultrasonic molecular imaging. Mol Imaging. Jul. 2004;3(3):135-48.
EP 11840660.2, Dec. 5, 2018, European Office Action.
PCT/US2018/020305, Apr. 23, 2018, Invitation to Pay Additional Fees.
PCT/US2018/020305, Jun. 25, 2018, International Search Report and Written Opinion.
U.S. Appl. No. 13/884,658, filed Sep. 24, 2013, Kheir et al.
U.S. Appl. No. 14/776,774, filed Sep. 15, 2015, Kheir et al.
U.S. Appl. No. 14/776,372, filed Sep. 14, 2015, Polizzotti et al.

* cited by examiner

Error bars = SEM

PROCESS FOR FORMING MICROBUBBLES WITH HIGH OXYGEN CONTENT AND USES THEREOF

RELATED APPLICATIONS

This application is a national stage filing under U.S.C. § 371 of PCT International application PCT/US2013/030392, entitled "PROCESS FOR FORMING MICROBUBBLES WITH HIGH OXYGEN CONTENT AND USES THEREOF," filed on Mar. 12, 2013, which claims priority under 35 U.S.C. § 119(e) to U.S. Provisional Application Ser. No. 61/621,261, entitled "PROCESS FOR FORMING MICROBUBBLES WITH HIGH OXYGEN CONTENT AND USES THEREOF," filed on Apr. 6, 2012, which are herein incorporated by reference in their entirety.

STATEMENT REGARDING FEDERALLY SPONSORED RESEARCH OR DEVELOPMENT

This invention was made with government support under grant number W81XWH-11-2-0041 awarded by the U.S. Department of the Army. The Government has certain rights in the invention.

FIELD OF THE INVENTION

This invention relates to apparatus and methods for forming microbubble formulations with high oxygen content for administration to patients.

BACKGROUND OF THE INVENTION

Every human cell requires a constant supply of oxygen to maintain cellular structure and homeostasis. This supply is primarily provided by hemoglobin, which carries inspired oxygen from the pulmonary capillaries to the tissues. In cases where a patient's lungs are unable to transfer adequate amounts of oxygen to circulating erythrocytes, severe hypoxia results and can quickly lead to severe organ injury and death.

Restoration of blood oxygen tension is paramount to resuscitation of the majority of pathophysiologic states. Some clinical states, such as lung injury, airway obstruction, and intracardiac mixing, exhibit hypoxemia and desaturation refractory to medical efforts to restore levels of oxygen saturation sufficient to limit ischemic injury. Ischemic injury may take place within minutes or seconds of insufficient oxygen delivery. In these conditions, low oxygen tension can result in end-organ dysfunction, failure, and mortality. The ability to augment oxygenation quickly and non-invasively would have dramatic implications on the morbidity and mortality from acute hypoxia, in addition to a number of other clinical situations.

Conventional attempts to restore oxygen levels in patients utilize supportive therapy of the patient's respiratory system, most commonly by way of mechanical ventilation. However, patients with lung injury, comprising a significant population of intensive care unit patients, have difficulty exchanging oxygen across damaged lungs or airways. This requires clinicians to increase ventilator pressures, often causing further lung injury and systemic inflammation. Significant morbidity and mortality has been associated with ventilator induced lung injury, and barotrauma to the lungs is often necessitated by inadequate systemic oxygen delivery. The ability to non-invasively supplement even small percentages of oxygen delivery may significantly reduce the morbidity of mechanical ventilation.

Furthermore, emergency efforts to deliver oxygen to a patient are often inadequate and/or require too long to take effect, either due to lack of an adequate airway or overwhelming lung injury. This results in irreversible injury to the brain and other organs. Initiation of rescue therapy in these patients is burdensome and time consuming, and is available only at a limited number of specialized health care centers.

SUMMARY OF THE INVENTION

Formulations containing a carrier and microbubbles encapsulating oxygen gas, and methods for making and using the formulations are described herein. The formulations are preferably manufactured by a process which includes a high shear homogenization step. In one embodiment, a precursor mixture comprising a carrier and at least one lipid, and optionally one or more stabilizing agents, is formed. In one embodiment, the precursor components are not premixed, rather they are introduced directly into the homogenizer. Then the precursor mixture is subject to high shear homogenization in an oxygen gas environment, for a sufficient period of time and at a sufficient speed to produce a microbubble suspension.

Preferably the lipid is a phospholipid, preferably 1,2-distearoyl-sn-glycero-3-phosphocholine (DSPC). Optionally the microbubbles also contain one or more stabilizing agents and/or excipients. Preferred stabilizing agents and excipients include but are not limited to the cholesterol, polyoxyethylene-polyoxypropylene (e.g., Pluronic F68, Poloxamer 188), Pluronic F108 (BASF), and combinations thereof.

The resulting microbubble suspension may be centrifuged to further concentrate the microbubbles. Alternatively, the microbubble suspension can be recycled through the homogenizer and concentrated sufficiently in this manner without the need for centrifugation. In an alternative embodiment, the homogenizer contains multiple stators, which provide multiple points of shear at which oxygen gas can be added to the suspension, such that a precursor mixture can be sufficiently concentrated in one pass through the homogenizer.

The resulting LOM formulation preferably has an oxygen content ranging from 50 to 99% (vol). In some preferred embodiments, the resulting LOM formulation typically has an oxygen concentration ranging from 65 to 80% (vol). In other embodiments, the resulting LOM formulation has an oxygen concentration of 15-20%.

In some embodiments, prior to administration to a patient, the viscosity of the LOM formulation is reduced to the desired viscosity, preferably similar to the viscosity of the patient's blood when measured under the same conditions. In one embodiment, the LOM formulation is diluted in a suitable carrier to the desired viscosity. Alternatively, the viscosity of the suspension can be lowered by the addition of viscosity lowering agents, such as mannitol, or by mechanical pre-shearing in a specialized catheter, for example.

BRIEF DESCRIPTION OF THE DRAWINGS

In FIGS. 4B and 4C, column height represents mean, error bars represent 95% confidence interval. (=P<0.01; *=P<0.001; n=8 samples per group).

DETAILED DESCRIPTION OF THE INVENTION

I. Definitions

Figure 1A:
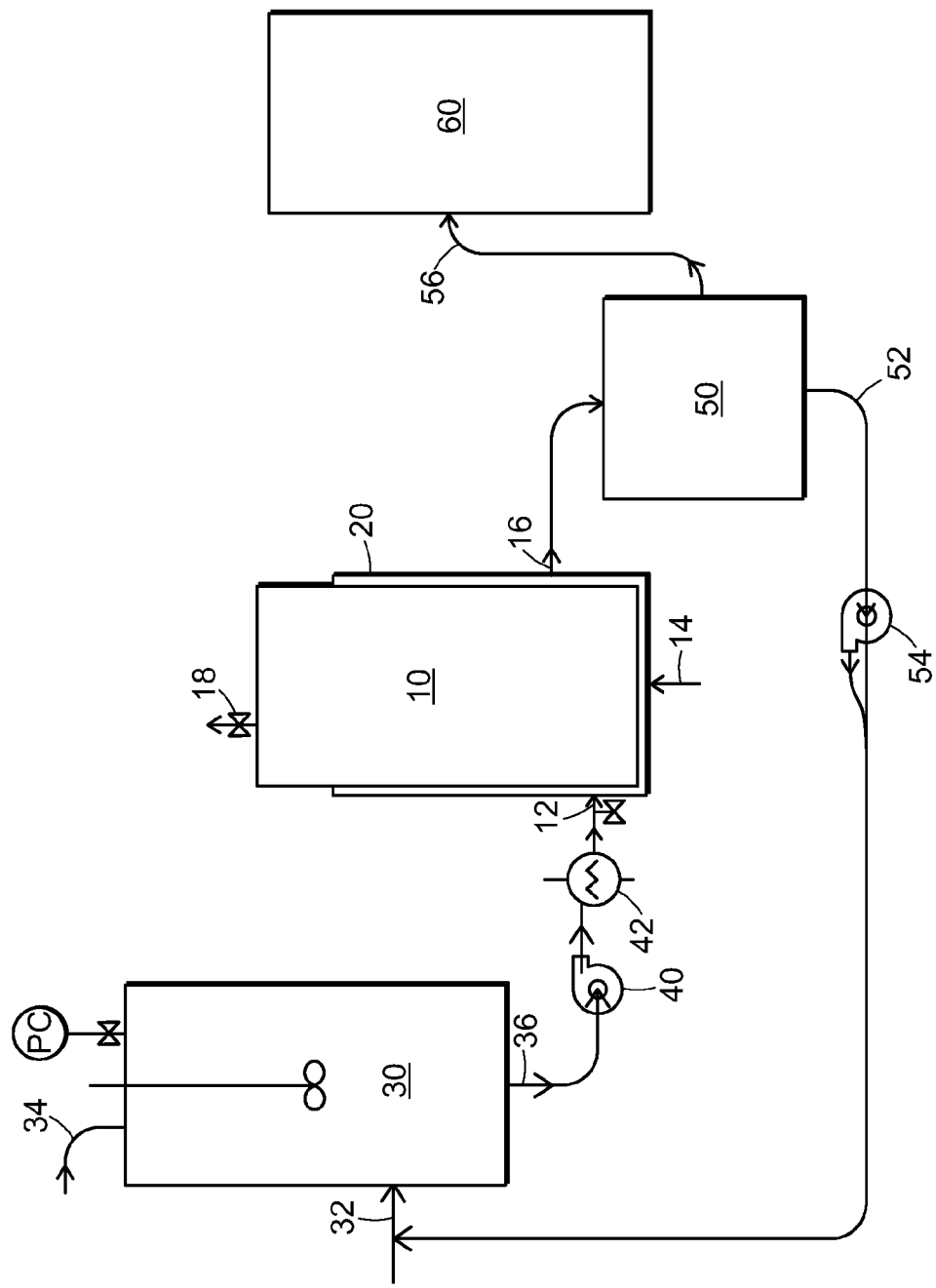
FIG. 1A is an exemplary benchtop set up for making a concentrated suspension of microbubbles containing oxygen.

"Base lipid" as used herein refers to the one or more lipids in the microbubble envelope that forms a border surrounding a core of oxygen gas, providing a large gas-blood interface due to its extremely high surface area-volume ratio, reduces surface tension, provides mechanical stability and prevents coalescence of multiple smaller bubbles into larger ones.

"Stabilizing agent(s)" as used herein refers to the one or more compounds included in the microbubble envelope that are capable of increasing the stability of the microbubble envelope compared to the stability of the same microbubble in the absence of the stabilizing agent, as determined by the shelf life of a bulk of microbubbles.

The term "Lipid-based oxygen microparticles" or "Lipid-based oxygen microbubbles" (LOM) is used herein to refer to microbubbles encapsulating oxygen. The LOMs are concentrated suspensions of microbubbles in a pharmaceutically acceptable carrier.

II. Method of Making Microbubbles and LOM Formulation

Microbubbles can be manufactured by sonication (Feinstein, et al., *J. Am. Coll. Cardiol.*, 3:14-20 (1984)), shearing (Dressaire, et al., *Science*, 320:1198-1201 (2008)), flow focusing (Di Carlo, et al., *Proc. Natl. Acad. Sci. U.S.A.*, 104:18892-18897 (2007)) or extrusion (Lindner, *Nat. Rev. Drug Discov.*, 3:527-532 (2004)). High shear homogenization is suitable for forming stable, mechanically formed microbubble preparations in large throughput. The microbubble formulations described herein are preferably manufactured by a process which includes a high shear homogenization step.

In one embodiment the LOM are made by mixing a lipid in a suitable carrier, for example, typically an aqueous solution, such as a saline solution, preferably phosphate buffer saline (PBS), to form a precursor mixture. The precursor mixture may be in the form of a suspension, dispersion, solution, or emulsion depending on the concentration and form of the lipid(s) in the carrier. Typically the precursor mixture is in the form of a suspension or dispersion. Optionally, the precursor mixture also includes at least one stabilizing agent, for example cholesterol.

In one embodiment, after the precursor mixture is formed, it is filtered, such as through a 0.4 micron filter, to remove large conglomerates of lipid.

Then oxygen gas is introduced to the precursor mixture under intense energy (such as, for example, sonication or shearing).

In a preferred embodiment, the precursor mixture is homogenized with a homogenizer at high shear (for example, a Silverson LSMA at 2,000-3,000 RPM for 2 minutes). This precursor mixture of hydrated lipids can be refrigerated and stored for 1 year or longer at 4° C. LOM suspensions are formed when a precursor mixture and oxygen ($O_2$) gas are introduced into a closed homogenizer (which allows for a 100% oxygen environment). In a preferred embodiment, the precursor mixture is infused at a rate of 0.25-5 liters/minute, preferably 2 liters/minute, and oxygen is co-infused with this mixture at one or more points at a flow rate of 20-1,000 mL/min, preferably at 60 mL/minute. For example, the oxygen gas may be delivered from a cylinder, through a flowmeter, and into a T-piece which co-infuses the fluid and gas phase into the stator of the mixer. Optionally, the precursor mixture is heated and then cooled prior to homogenization.

Figure 10:
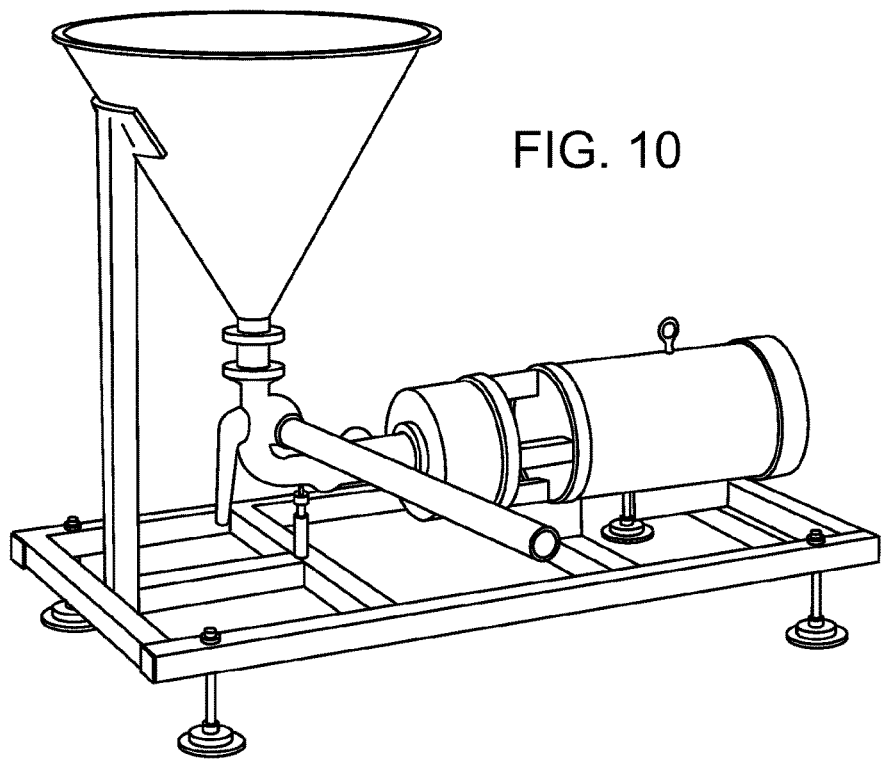
FIG. 10 is a schematic of a homogenizer into which the precursor components can be fed directly without premixing. The homogenizer illustrated in FIG. 10 may be used as to hydrate powdered lipids by adding fluids to the mixture.

In an alternative embodiment, the precursor components are fed directly into a homogenizer without premixing, or into serial homogenizers. In this embodiment, the first homogenizer may hydrate powdered lipids by adding fluids to the mixture (see, e.g., FIG. 10), and pump the hydrated lipids (precursor components) directly into a second chamber (or a second homogenizer) which contains one or more inlets for gas and/or microbubble precursor components to be fed into the homogenizer. Each inlet may correspond to a rotor stator to allow for a one-step manufacturing process that does not require additional purification or concentration steps.

This manufacturing process produces a suspension of microbubbles which may be refined by a size isolation step (utilizing floatation), then concentrated by centrifugation. These latter two steps are optional, and are preferably omitted, when the characteristics of the homogenizer and the flow rates of gas and precursor components or precursor mixture produce a microbubble suspension having an oxygen concentration ranging from 50% to 99%, preferably 70 to 99%, more preferably 65-80%, 80-99% oxygen, more preferably 90% or greater.

Preferably, the entire system used in the manufacture of the LOM formulation is sterilizable and closed to the environment such that the $PO_2$ of the resulting LOM formulation is above 700 mmHg, preferably approaching 760 mmHg.

A. Modifications to the Manufacturing Process Affect the Properties of the Resulting LOM Suspension The properties of the resulting microbubbles are influenced by a number of manufacturing parameters. First, the size of the LOMs can be controlled by the characteristics of the rotor stator (e.g. the smaller the size of the pores within the rotor stator, the smaller the resulting particles), the rotational speed of the rotor, the number of passes LOMs make through the system prior to being complete (i.e. the number of stators placed in series), the rate of fluid and gas infusions into the system (slower infusion rates and higher shear rates yield smaller particles), and concentration of lipid within the fluid phase passing over the rotor stator. As the fluid-microbubble mixture becomes increasingly concentrated, it becomes more viscous and difficult to move. In the manufacturing process, if a fluid is recycled again and again, it becomes more difficult to pump. Then standard pumps, such as roller pumps, are unable to maintain a constant infusion rate. In this instance, it is helpful to increase the speed of the roller pump or to push the viscous fluid through the system using pressurization of the vessel. Preferably, for embodiments which require the liquid phase to be recycled again and again through a vessel and a homogenizer, the return holding vessel can be maintained in a pressurized state using a pressure regulator and oxygen gas.

Second, the temperature of the gas and fluid phase are important in determining the size of LOMs. For example, microbubbles can be made smaller by increasing the temperature of the components during manufacture and subsequently cooling them. In one setup, the stability of the LOMs can be increased, and the yield of LOMs increased, by cooling the LOMs following their manufacture, such as by passing them through a heat exchanger which is cooled, such as to 2° C. However, the effect of this step is small and likely unimportant. Furthermore, rapid sequential heating and cooling of freshly formed LOMs may create small, localized defects in the lipid layer (i.e. density defects) of the microbubbles, which increases their permeability.

B. Properties of the Resulting LOM Suspension

The external, continuous liquid phase of the LOM suspension typically contains stabilizing agents and/or excipients.

LOMs prepared according to the method described herein have high oxygen content, from 50% to 99%, preferably 70 to 99%, more preferably, 80-99% oxygen, more preferably 90% or greater.

The resulting LOM formulation is stable at temperatures of 4, 22 and/or 37° C. for at least one week, preferably for at least 28 days, more preferably for at least 100 days.

C. Components for Manufacturing the LOM Suspension a. Homogenizer

Laboratory homogenizers are high-speed, high-shear mixers that reduce and homogenize samples through maceration, cutting, and blending. Product specifications for laboratory homogenizers include viscosity of the fluid, capacity (volume of product that the homogenizer can accommodate), feed rate (product flow over a given period of time), motor speed, motor power, pressure range, and operating temperature. Additional characteristics, such as pH concentration and specific gravity, are also important considerations. Optionally, the homogenizer includes an integral cooling element.

Any suitable homogenizer may be used, such as a fluidized bed, rotor-stator, or ultrasonic (or vibrational) homogenizer. In the preferred embodiment, the homogenizer is a rotor-stator homogenizer. Rotor-stator homogenizers are single-shaft mixers with an impeller which rotates in close proximity to a stationary housing (here referred to as a rotor stator). The rotor imparts high shear forces mechanically, while the stator directs the flow.

Suitable bench-scale homogenizers include Silverson homogenizers, such as the L5M-A laboratory mixer and the Verso in-line Mixer. A schematic of a section of the Silverson Verso homogenizer is shown in FIG. 1D (copied from the Users' Manual provided with the Silverson Verso).

The method described herein can be scaled up using production scale equipment, also manufactured by Silverson. Preferably the homogenizer is integrated in the process, such as by using an in-line mixer. An exemplary benchtop set up, which is representative of the set up used to form the microbubbles tested in the Examples, is illustrated in FIG. 1A. This set up can be modified and scaled up for increased production of the microbubble formulations.

As illustrated in FIG. 1A, the homogenizer (10) contains at least one inlet for the precursor mixture (12), at least one gas inlet (14), at least one microbubble outlet (16), and at least one vent (18). Preferably the homogenizer is temperature controlled, such that it can be maintained at a desired temperature. In one embodiment, the homogenizer is surrounded by a cooling jacket (20), preferably maintained at approximately 2° C., to control the homogenizer temperature. Preferably, the homogenizer contains one or more gas inlets which introduce oxygen gas directly within the rotor stator and a separate inlet for the precursor mixture, which contains at least one hydrated lipid.

The precursor components are preferably premixed, in an oxygenated feed vessel (30), which contains at least one inlet for the lipid, carrier, and other precursor components (32), at least one inlet for oxygen gas (34), and at least one outlet (36) for the precursor mixture that is then fed to the homogenizer. In embodiments which require more than one pass through the homogenizer, it is preferred that the outlet port of the homogenizer be attached to a cooling bath (54), which then returns to the feed vessel (30). Preferably the pressure of the feed vessel is controlled via a pressure controller and/or pressure relief valve (38). In another embodiment, the precursor mixture is fed into the precursor inlet, without premixing with the oxygen gas (not shown).

Optionally, the precursor mixture is pumped via a suitable pump (40) at the desired flowrate into the inlet for the homogenizer. In another embodiment, optionally, the homogenizer produces a vacuum which draws fluid into itself, which obviates the need for a pump. Prior to entering the homogenizer, in some embodiments, the precursor mixture is either heated or cooled via a suitable heat exchanger (42) to the desired temperature. In some embodiments, the precursor mixture is heated, followed by a cooling step prior to entering the homogenizer.

After the homogenizer runs for a suitable period of time at a suitable rate, typically ranging from 2,000 to 25,000 RPM, preferably ranging from 7,000 to 8,000 RPM, the microbubbles exit the homogenizer via the microbubble outlet (16). The fluid phase is infused at a suitable rate, such as approximately 1 liter per minute. The gas phase is infused at a suitable rate, such as 60 mL/minute (up to 1,000 mL/min). Optionally, the fluid is recycled through the system for a suitable time period, such as from approximately 2 to 35 minutes, preferably approximately 10 minutes, more preferably approximately 12 minutes. Microbubbles are then collected in a collection vessel (60). Any remaining or microbubbles that are larger than the desired size range are then recycled (52) back to the feed vessel, and are typically pumped with a suitable pump (54) to maintain the desired recycle flowrate. Alternatively, one large homogenizer can be used to manufacture size-limited microbubbles using several gas inlets in series. Alternatively, the homogenized suspension can be pumped through several homogenizers in series, each of which would add to the gas fraction and avert the need for centrifugation or recycling as described.

Optionally, at some point in the recycling process, the microbubbles are centrifuged at a sufficient force and for a sufficient period of time in a centrifuge (50) to further concentrate the microbubbles. This step is most efficiently performed when the recycled microbubble suspension is approximately 30-50 volume %. The centrifuging step is sufficient to separate a microbubble suspension phase from the liquid phase, where the concentrated microbubble suspension phase contains microbubbles having a size of mostly 10 microns or lower. The liquid phase contains any remaining precursor mixture and lipids. Microbubbles that are excessively large, e.g. exceeding 20 microns in diameter, are unstable and are broken by a modest centrifugal force (i.e. 500-1,000 RPM for 10-20 minutes).

Following the concentration step by centrifugation, concentrated microbubbles (also referred to herein as the LOM formulation) are collected into a syringe or a supersyringe (or other gas-tight container) for further use or distribution.

1. Number and Size of Stators

The number and size of the stators in the homogenizer affects the efficiency of the process. The size and shape of the pores within each rotor stator, combined with the shear rate of the rotor, determines the size of the microbubbles. Smaller pores, oblong shapes, and a higher shear rate yield smaller particles. Increasing the number of rotor-stators permits (a) re-shearing of large microbubbles, creating smaller microbubbles and affording a more favorable size distribution and (b) allows several points at which oxygen gas can be introduced into the system for incorporation into the LOM formulation. This allows a more concentrated final product without the need for centrifugation. In the Examples disclosed herein two rotor-stators were used in the Verso homogenizer to form the microbubbles. However one rotor-stator may be used, or two or more rotor-stators may be used to form the microbubbles, in one large homogenizer or, alternatively, by attaching several homogenizers in series.

2. Workheads and Screens

The workhead is attached to the distal end of the stator, to allow the same homogenizer to perform different operations, including emulsifying, homogenizing, disintegration, dissolving, dispersing, blending, particle size reduction (e.g. micronization), and/or de-agglomerating. In the Examples disclosed herein, the workhead used was a two stage ultrafine emulsor screen (Silverson Fine Mesh for both the inner and outer emulsor screens).

3. Gas and Liquid Flow Rates into the Homogenizer

The rate at which the liquid precursor inlet flows into the homogenizer and the rate at which the gas, typically oxygen gas, is fed to the homogenizer also affect the properties of the resulting microbubbles and LOM suspension. Preferred feed for oxygen gas range from about 25 mL/min to 1 L/min. In the Examples, the precursor mixture was fed at a rate of 1 L/min; and the oxygen gas was fed at a rate of 0.25 to 1 L/min.

4. Time for Recycle

The suspension described in the Examples was recycled as above for 20 minutes, meaning that a 1 liter suspension began with 0% gas fraction and ended up with a 1,000 mL gas fraction, approximately a 50 volume % oxygen suspension. Under some conditions, it is possible to continue recycling and create an 85-90 volume % oxygen suspension without centrifugation. However, as the LOM suspension becomes more concentrated with oxygen gas, it becomes more viscous. For example, as LOM suspensions approach 75-80 volume % of gas, the viscosity typically increases exponentially and therefore the suspension flows more slowly into the homogenizer. Additionally, free gas can become trapped within viscous fluid and not be adequately incorporated into the LOM suspension. Therefore, optionally, the recycled LOM suspension may be pressurized to provide a sufficient flowrate to incorporate additional oxygen gas into the LOM suspension. Alternatively or additionally, the flow rates of gas into the homogenizer may be decreased to ensure that the oxygen is incorporated into the microbubbles and prevent or reduce the likelihood that it is trapped in the fluid phase of the suspension.

b. Mixer

In one embodiment, the components of the precursor mixture are mixed prior to entry into the homogenizer. As shown in FIG. 1A, a mixing element may be integrated in the feed vessel (30).

Feed Vessel for LOM Manufacture

The feed vessel (30) may contain one or more features to facilitate passive flow of the precursor components into the homogenizer, such as by selecting a geometry which takes advantage of the force provided by gravity to transfer the liquid precursor components out of the feed vessel and into the homogenizer.

Figure 1B:
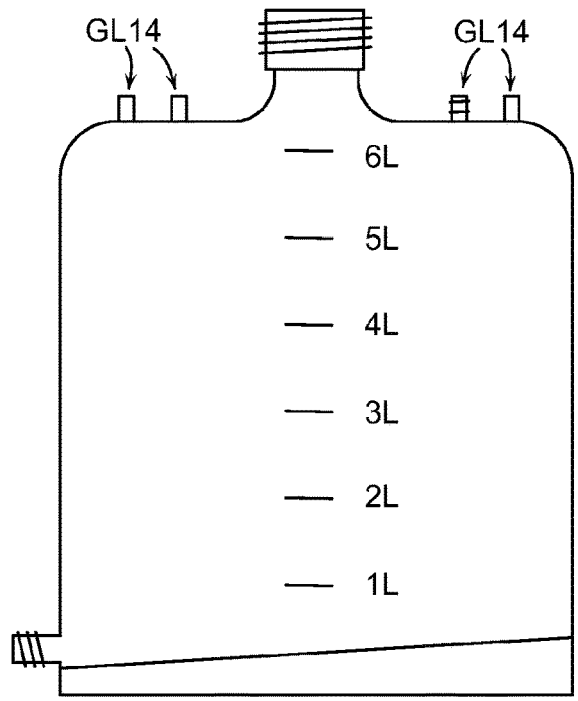
FIG. 1B is a schematic of a container designed for the manufacture of LOMs.
Figure 1C:
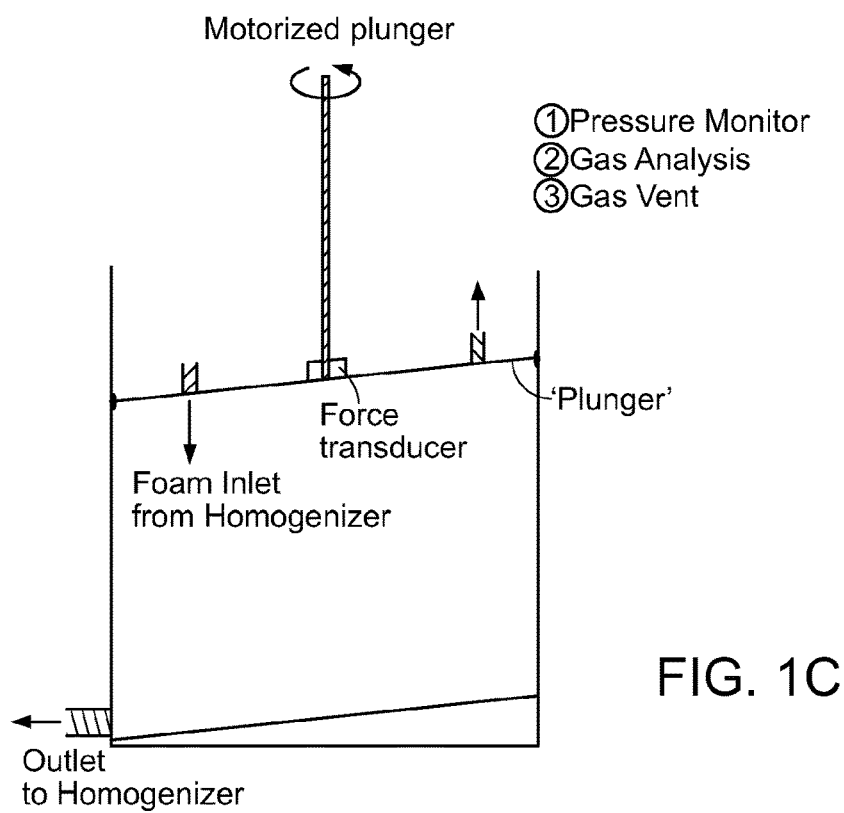
FIG. 1C is an alternative embodiment of a container designed for the manufacture of LOM.
Figure 1D:
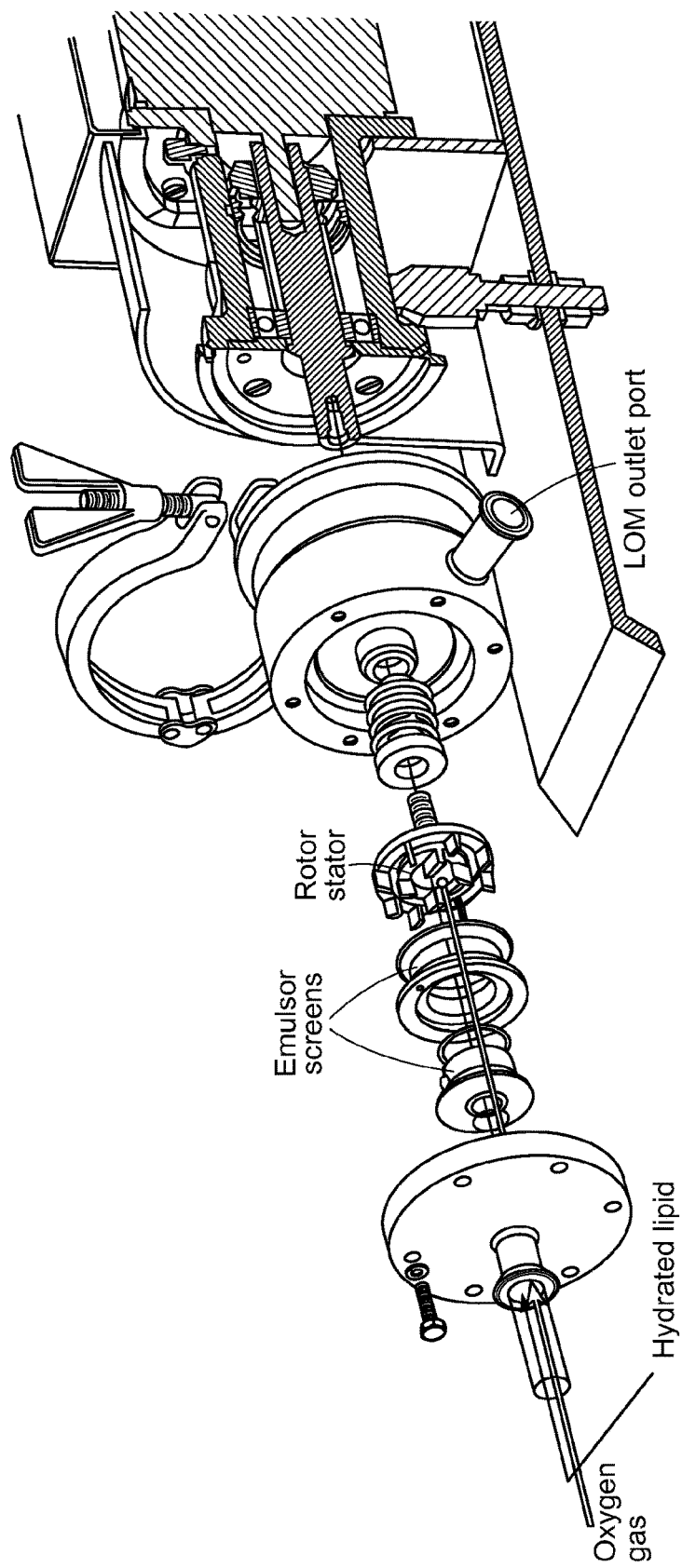
FIG. 1D is a cross-sectional, expanded view of a Silverson Verso homogenizer that can be used to homogenize the aqueous and gaseous phases to manufacture LOMs.
Figures 2A, 2B, 2C, 2D:
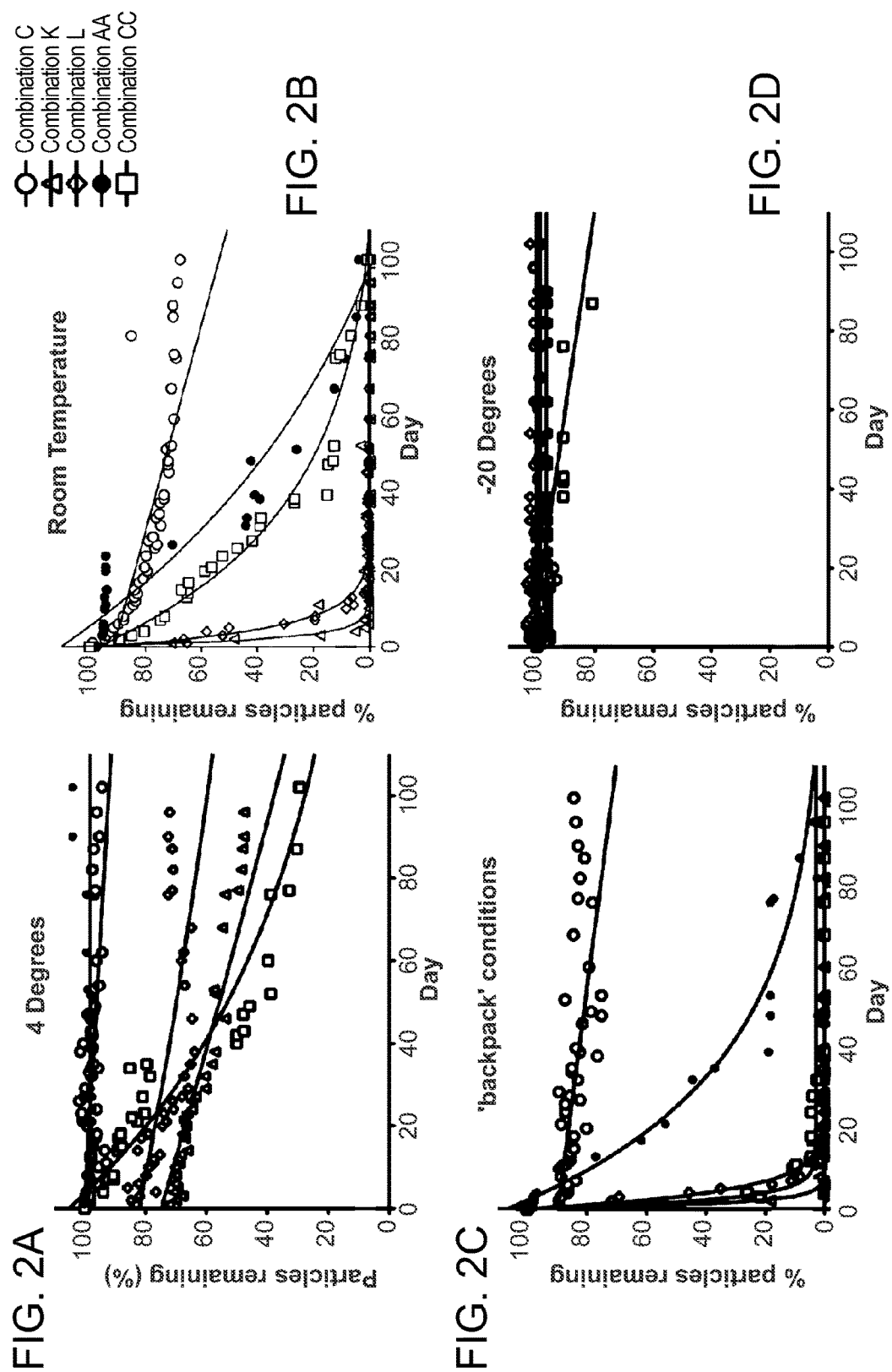
FIG. 2A is a graph showing stability of five candidate LOM combinations (C, K, L, AA, CC in Table 1) at 4° C.
FIG. 2B is a graph showing stability of five candidate LOM combinations (C, K, L, AA, CC in TABLE 1) at room temperature.
FIG. 2C is a graph showing stability of five candidate LOM combinations (C, K, L, AA, CC in Table 1) under 'backpack' conditions (i.e. heated to 30° C., 100% humidity and continuous motion).
FIG. 2D is a graph showing stability of five candidate LOM combinations (C, K, L, AA, CC in Table 1) at −20° C.

Exemplary feed vessels are illustrated in FIGS. 1B and 1C. Referring to FIG. 1B, the feed vessel (30) features an internally slanted base which allows all of the fluid phase to exit through the bottom port. The feed vessel could have alternative geometries, yet still ensure that all of the fluid phase exits the container and is fed to the homogenizer. For example, in place of a slanted bottom, the container could have a curved bottom, with a port in the bottom (not shown in figures). At the top of the vessel are a plurality, preferably four, gas-tight ports, which are used to (a) wash the vessel with oxygen gas, (b) monitor the oxygen gas fraction within the vessel, (c) recycle LOMs into the vessel and (d) monitor the pressure within the vessel. The outlet at the base of the vessel is attached to a roller pump (Sarns 8000 Roller Pump, 3M Health Care, Ann Arbor, Mich.), which is then used to 'feed' the homogenizer. Alternatively, the vessel can be placed above the homogenizer, at a sufficient height, e.g. such as four feet, to use the force of gravity to provide a sufficient flow rate of the precursor fluid into the homogenizer.

c. LOM Suspension Container

An exemplary LOM suspension container is illustrated in FIG. 1C. This container is designed to contain the LOM suspension within its cavity and to contain virtually no free gas. The vessel is a tall column with a plunger which can run the length of the column, attached to a motorized screw which moves the plunger, attached to a force transducer. At the beginning of manufacture, the chamber is filled with the aqueous phase, and is purged of all gas. The homogenizer can be primed by downward force on the plunger by the motorized screw until fluid returns back into the LOM suspension inlet. All gas entering from the prime will exit the gas vent, fitted with a one-way valve. At this point, the system would be closed, such that pressure on the force transducer would increase rapidly with increasing downward force by the motorized plunger, and the homogenizer could be started automatically. As the fraction of gas-filled microbubbles begins to increase, the fluid within the chamber increases in volume, exerting a small force on the force transducer. The motorized plunger move upwards slowly to relieve some of this pressure, permitting the LOM suspension within the chamber to maintain a slightly pressurized state. As the LOM suspension becomes increasingly viscous, the force exerted by the plunger increases, with the goal of 'feeding' the homogenizer with a constant volume of the aqueous phase.

In this way a 90-95 volume % oxygen suspension could be made while avoiding the problem of cavitation. One additional modification which may be useful is to create a non-pressurized oxygen reservoir which could attach to the T-piece found in the homogenizer. This would permit oxygen to be 'sucked' into the homogenizer, but not forced into it, which would decrease the likelihood of free gas being formed as microparticle gas fraction increased from the 60-90 volume % range.

d. Heat Exchanger

One or more heat exchangers may be included in the process to heat or cool the precursor fluid, prior to entering the homogenizer. Optionally, additional heat exchangers are included in the process, as needed, to heat or cool the inlets or outlets prior to the next step in the process.

e. Pumps

One or more pumps may be included in the process to feed the inlet streams, recycle stream, and/or outlet streams to the next step at the desired flowrate. Roller pumps may not be useful for this process because the fluid is compressible. It is preferable to incorporate compression-decompression pumps to move the fluid in this process. Alternatively, the shear created by the homogenizer may create sufficient flowrate of fluid, thereby obviating the need for other pumps.

f. Oxygen Supply

Typically, oxygen gas is fed into the homogenizer. Preferably, oxygen is also fed to the feed vessel. Optionally, the entire process is performed in a closed oxygenated environment. Suitable valves to release pressure and oxygen, as needed, are included in the various vessels in the system. Additionally controls to regulate temperature and pressure are included, as needed, to control the temperature and pressure of the various components in the process. It may be necessary to create oxygen gas on site rather than using pre-bottled medical oxygen gas, which contains a small number of impurities.

g Optional Components

The amount of oxygen in the microbubble suspensions can be increased by centrifugation. In one embodiment, a centrifuge (50) is included in the system to further concentrate the oxygen-containing microbubbles, prior to or after collection in the collection vessel.

1. Isolating LOM

A rapid and simple method for concentrating and isolating sub-populations of oxygen-containing microbubbles was previously developed and is described in U.S. Published Application No. 2009/0191244 by Kheir, et al. This method involves the use of differential centrifugation to isolate size-selected microbubbles based on their migration in a centrifugal field.

The relative centrifugal force (RCF) needed for a microbubble size class to rise through the column of length L for a fixed centrifugation time can be calculated. For example, Stokes' equation for the rise velocity of a buoyant particle relative to the bulk fluid under creeping flow conditions can be used as follows:

$$u_i = \frac{2(\rho_2 - \rho_{1i})}{9\eta_2} r_i^2 g, \qquad \text{(Eq. 1)}$$

where subscript i refers to the microbubble size class, $r_i$ is the microbubble radius and g is the gravitational (centrifugal) acceleration measured in RCF. (see Kvale, et al., "Size fractionation of gas-filled microspheres by flotation", *Sepa-* rations Technology, 6(4):219-226 (1996)). The effective viscosity, $\eta_2^*$, of the microbubble suspension can be calculated using Batchelo and Green's correlation for the modified fluid viscosity:

$$\frac{\eta_2^*}{\eta_2} = 1 + 2.5\Phi + 7.6\Phi^2, \quad \text{(Eq. 2)}$$

$$\Phi = \sum_{i=1}^{N_d} \Phi_i, \quad \text{(Eq. 3)}$$

where $\Phi$ is total the microbubble volume fraction for $N_d$ size classes. (Batchelo & Green, "Determination of Bulk Stress in a Suspension of Spherical-Particles to Order C-2", *J. of Fluid Mech.*, 56: 401-427 (1972).) Equations 1-3 can be used to calculate the strength of the centrifugal field (in RCF) for a given initial size distribution, time period and syringe column length.

In one embodiment, the centrifugation step is applied after homogenization and recycling. A 30-60 volume gas/volume suspension results from homogenization and recycling. This suspension is collected within syringes, such as 140 mL syringes, in a gas-tight manner, and then centrifuged for a suitable period of time, such as 10 minutes, at 500-1,000 RPM. This results in a composition with three phases. Furthest from the centrifugal force (toward the center of the centrifuge) is free oxygen gas, likely a result of trapped gas within the diluent fluid (i.e. never incorporated into microbubbles) or larger, more fragile microbubbles which break as a result of the mild centrifugal force. The middle section contains a large, concentrated microbubble suspension of a polydispersed size distribution. Finally, there is a fluid phase which contains tiny, non-buoyant microbubbles (smaller than 1 micron diameter, with a small volume of gas), lipid and diluent fluid. This fluid is discarded or recycled and the concentrated LOM formulation is collected.

Alternatively, this process can be performed on a continuous basis using a commercially available continuous centrifuge, or using a differential phase separator utilizing differential centrifugal forces such as that used to separate different portions of blood (e.g. Sorvall CC40 continuous centrifuge by Thermo Fisher).

Using this method, the amount of gas (e.g. oxygen) in the microbubble suspensions can be increased 2-fold to 10-fold, or by even greater amounts, and standardly results in a 90-98 volume % suspension.

III. Microbubble Formulations

The compositions described herein contain concentrated microbubbles suspended in a suitable carrier, and also referred herein to as LOM formulations. The microbubbles encapsulate one or more gases, preferably oxygen, for administration to patients, tissues or organs in need of treatment. Preferably there is no perfluorocarbon in the formulations.

A. LOM Formulations

The LOM formulation is a concentrated suspension of microbubbles in a pharmaceutically acceptable carrier. The LOMs described herein exist in a complex fluid containing a gas phase and a fluid phase which contains one or more lipid components. LOMs are composed of lipid excipients which are generally recognized as safe (GRAS) by the US FDA.

Typical viscosities for the LOM formulations range from 0.1 to 0.6 Pa*s when measured at 25° C. using a Rheometer with 40 mm parallel plate geometry (such as, AR 2000ex, TA Instruments, New Castle, Del.) at a shear rate of 2,000/second. The viscosity of the LOM formulation prior to administration to a patient is preferably statistically similar (p>0.05) to the viscosity of human blood in the same conditions (temperature, shear rate, shear stress).

a. LOM Oxygen Content

Additionally, the preferred manufacturing process produces a LOM suspension containing about 50% (vol) to about 99% (vol) oxygen encapsulated in the microbubbles.

LOMs suspensions prepared as described herein contain 3-4 times the oxygen content of arterial blood, which is 18 mL oxygen/dL blood. Preferably, LOM suspensions prepared according to the method described herein contain greater than 50% (vol), more preferably greater than 60% (vol), more preferably greater than 70% (vol), more preferably greater than 80% (vol), and more preferably 90% (vol) or greater oxygen. The most preferred embodiment provides LOM suspensions with gas fractions between about 60 and about 80 volume % when the microbubbles are administered to a patient. For some indications however, LOM suspensions with lower oxygen content may be desired. In these embodiments, the LOM suspension can contain between 15-20% (vol) oxygen.

Although the suspension can be manufactured to contain 95 mL of oxygen gas per 100 mL of suspension (i.e., 95% (vol) oxygen), LOMs at this concentration are exceedingly viscous to be administered via injection (IV, bolus, or intraosseous). The LOM suspension may be diluted with a suitable volume of a carrier prior to administration to a patient to achieve the desired oxygen concentration, and resulting desired rheologic properties (e.g. viscosity, flowability). For example, the LOM suspension can be diluted to gas fractions between 60 and 80 volume % (60-80 mL oxygen gas per 100 mL of suspension). This decreases the viscosity of the LOM suspension to approximately that of human blood under high shear conditions (for example, at 2,000/sec).

b. Microbubble Size and Size Distribution

Typically, the majority of microbubbles in the LOM formulation are 10 microns or smaller. Less than 5% of particles exceed 10 microns in diameter, and preferably all of the particles have a size of 10 microns or less.

The microbubbles in the LOM formulation to be administered to a patient, or organ or tissue, are polydisperse by design, containing particles of varying size within the size range of 10 microns or smaller. This allows tight packing of the deformable particles in the LOM formulation, particularly during storage.

The lipid monolayer surrounding the gas phase provides a Laplace overpressure (which favors diffusion of gas out of the particle), and prevents a direct blood-gas interface (which prevents blood trauma). Their small size optimizes the surface area volume ratio, creating a large surface area for gas transfer to erythrocytes in circulation.

The manufacturing process described herein preferably produces microbubbles predominantly within the size range of 1 to 10 microns, with greater than 90% of the microbubbles within this size range. Preferably, the mean size for the microbubbles is 8 microns or less. More preferably, greater than 80%, more preferably greater than 90%, more preferably greater than 95% of the microbubbles in the formulation have a diameter that is 10 microns or smaller, preferably 8 microns or less, more preferably between 2 and 8 microns. Some formulations contain approximately $3 \times 10^{10}$ microbubbles/mL The size of the microbubbles can be determined by any suitable device, such as an Accusizer® or a Multisizer® III. While the Accusizer® measures size based on light obscuration and scattering, the Multisizer® utilizes electrical impedance sensing of the volume of electrolyte displaced by the microbubble as it passes through an orifice.

Microscopy can be used for direct visual inspection of the microbubbles in the suspension.

Flow cytometry can be used to further characterize the polydisperse microbubbles. Forward-(FSC) and side-(SSC) light scattering measurements can be taken. These measurements can also be used to correlate the data obtained using the Accusizer® or Multisizer® III to better understand the size distribution of the microbubbles.

c. Microbubble Envelope

The microbubbles contain a lipid envelope formed of at least one base lipid and at least one stabilizing agent and a gas core. The envelope is in the form of a monolayer or multilayer, preferably in the form of a monolayer.

The envelope may contain a variety of different amounts of base lipids and stabilizing agents. An optimum ratio of stabilizing agents to base lipids, which lies between a minimum ratio needed to have sufficient amounts of stabilizing agents to aid in lipid adsorption, shield the surface of the microbubble and prevent coalescence and a maximum ratio where lateral repulsion forces due to the presence of the stabilizing agent begin to significantly disrupt packing of the base lipid, may be determined experimentally.

Microbubbles containing a lipid envelope are described for example, in U.S. Published Application No. 2009/0191244 by Kheir, et al., the contents of which are herein incorporated by reference. Generally the lipid envelope contains at least one base lipid and at least one stabilizing agent. Optionally, at least a portion of the stabilizing agent forms a protective film on the outer surface of the envelope.

i. Lipid Envelope

A variety of lipids may be used to form the lipid envelope. The lipids may be natural or synthetic. Suitable lipids include phospholipids, fatty acids, triacyl glycerols, sphingolipids, terpenes, and waxes.

The lipids may have acyl chains of varying lengths and degrees of saturation. In some embodiments, the lipid is a long-chain lipid, preferably a saturated diacyl phosphatidylcholine (Di-$C_n$-PC, where n is between 12 and 24, preferably where n is 16 or 18), which imparts low surface tension, high stability against envelope dissolution, and low gas permeability prior to administration in vivo. Suitable lipids include phosphocholines, phosphoglycerols, phosphatidic acids, phosphoethanolamines, and phosphoserines. Examples include 1,2-Dilauroyl-sn-Glycero-3-Phosphocholine (dilauroylphosphatidylcholine, DLPC), 1,2-Dimyristoyl-sn-Glycero-3-Phosphocholine (dimyristoylphosphatidylcholine, DMPC), 1,2-Dipentadecanoyl-sn-Glycero-3-Phosphocholine (dipentadecanoylphosphatidylcholine, DPDPC), 1,2-dipalmitoyl-sn-Glycero-3-Phosphocholine (dipalmitoylphosphatidylcholine, DPPC), 1-Myristoyl-2-Palmitoyl-sn-Glycero-3-Phosphocholine (1-myristoyl-2-palmitoylphosphatidylcholine, MPPC), 1,2-Dimyristoyl-sn-Glycero-3-[Phospho-rac-(1-glycerol)] (DMPG), 1,2-Dimyristoyl-3-Trimethylammonium-Propane, 1,2-distearoyl-sn-glycero-3-phosphocholine (DSPC), cholesterol and its derivatives, fatty acids, fatty alcohols, and fatty esters. Preferably the envelope contains one or more phospholipids, for example, DSPC.

a. Acyl Chain Length

The number of carbons in the acyl chains of the lipids may range from 10 to 24 carbons. The average acyl chain length of the lipids in microbubbles typically ranges from 10 to 24 carbons. For example, the average acyl chain length of the lipids may be 20, 18, 16, 14, 13, or 12 carbons. The envelope may include one or more synthetic lipids with asymmetric acyl chains, where one acyl chain is longer than another.

Lipids with longer acyl chain lengths are generally preferred compared to lipids with shorter chain lengths. Generally lipids with longer chain lengths produce more microbubbles with a greater shelf life. However, the chain length should not be too long, decreasing the rate of gas release in vivo. In additions, longer chained lipids (e.g. 24-carbon vs. 16-carbon) are generally more resistant to oxygen passage. Resistance to gas release is also increased in walls composed of saturated (i.e. no double bonds) versus unsaturated lipids. Lipids with one or more double bonds contain kinks in the acyl chains due to the presence of the double bonds, which creates irregularities in the packing geometry, and thereby allows for gas to transfer out of the microbubble more rapidly.

Increasing or decreasing lipid acyl chain lengths in the microbubble may result in changes in the shearing properties of the envelope.

Stabilizing Agents

Stabilizing agents include any compound or composition that aids in the formation and maintenance of the bubble membrane by forming a layer at the interface between the phases. Suitable stabilizing agents include surfactants, detergents, wetting agents, emulsifiers and sterols, all of which are well known in the art.

In one embodiment, a stabilizing agent contains a hydrophobic moiety, which associates with the phospholipid layer, and a hydrophilic component, which interacts with the aqueous phase and minimizes the energy of the microbubble, thereby enabling its stability. For example, the stabilizing agent could be is a hydrophilic polymer attached to a hydrophobic anchor via one or more covalent bonds. Preferably the hydrophobic anchor is a lipid. The hydrophobic anchor may be an alkyl group, in the form of a single chain or multiple chains. Typically the alkyl group is 12 to 24 carbons in length. Alternatively, hydrophobic anchors such as sterols, or polymers such as polycaprolactone may be used.

An example of a useful stabilizing agent is polyethylene glycol (PEG). Typical weight average molecular weights for PEG range from about 550 Da to 5,000 Da. Alternatively, other molecules can be in place of PEG. Alternatives include polypropylene glycol, polyvinyl alcohol, poly-N-vinyl pyrrolidone (PVP) and copolymers thereof, mixed polyalkylene oxides having a solubility of at least one gram/liter in aqueous solutions, such as some poloxamer nonionic surfactants, neutral water-soluble polysaccharides, including dextran, Ficoll, and derivatized celluloses, non-cationic poly (meth)acrylates, non-cationic polyacrylates, such as poly (meth)acrylic acid, and esters amide and hydroxyalkyl amides thereof, and combinations thereof.

Preferred stabilizing agents include polyoxyethylene-polyoxypropylene, Pluronic F108 and cholesterol. Cholesterol was investigated to evaluate its influence on the LOM formulation stability by using a high shear homogenizer, as described in the Examples. Without being bound by theory, it is believed that cholesterol decreases the diffusion coefficient of lipids in phosphatidylcholine membranes and thereby affects the mobility as well as the permeability of the membrane. In this way, cholesterol may be used to stabilize microbubble envelope.

iii. Other Excipients

Additional excipients that can function as viscosity reducing agents can be included in the LOM formulations described herein in order to decrease the viscosity of the formulation to a desired level. Mannitol can be used as a viscosity lowering agent for very concentrated formulations.

Preferably the microbubbles are formed from one or more phospholipids, in combination with cholesterol, polyoxyethylene-polyoxypropylene (e.g., Poloxamer 188), hydroxyethyl starch (HES), gelatin, Pluronic F108 (BASF), sodium deoxycholate (Na-DOC), polyvinylpyrrolidone (PVP), or glycerol, or combinations thereof. Various amounts of these components were combined to form microbubbles according to the method described herein. Table 1 lists the components for each formulation.

Preferred formulations based on stability, size-distribution and biocompatibility are Formulations C, K and L described below in Table 1, with Formulation C being particularly preferred.

TABLE 1

Components in Exemplary Oxygen-containing Microbubble Formulations

| Formulation | Component 1 | Component 2 | Component 3 | Component 4 | Component 5 |
|---|---|---|---|---|---|
| A | DSPC 10 mg/mL | F68 10 mg/mL | Cholesterol 5 mg/mL | | |
| B | DSPC 10 mg/mL | | | | |
| C | DSPC 20 mg/mL | Cholesterol 10 mg/mL | | | |
| D | DSPC 20 mg/mL | F108 20 mg/mL | Cholesterol 10 mg/mL | PVP 20 mg/mL | |
| E | DSPC 10 mg/mL | F68 20 mg/mL | Cholesterol 10 mg/mL | | |
| F | DSPC 20 mg/mL | F108 20 mg/mL | NaDOC 2 mg/mL | | |
| G | DSPC 20 mg/mL | F108 20 mg/mL | NaDOC 2 mg/mL | F68 20 mg/mL | |
| H | All components of G | Cholesterol 10 mg/mL | PVP 20 mg/mL | | |
| I | DSPC 10 mg/mL | F68 20 mg/mL | PVP 20 mg/mL | | |
| J | DSPC 10 mg/mL | PVP 20 mg/mL | NaDOC 2 mg/mL | | |
| K | DSPC 20 mg/mL | F68 20 mg/mL | PVP 20 mg/mL | | |
| L | DSPC 20 mg/mL | F108 20 mg/mL | PVP 20 mg/mL | Cholesterol 10 mg/mL | |
| M | DSPC 10 mg/mL | F108 20 mg/mL | NaDOC 2 mg/mL | | |
| N | DSPC 10 mg/mL | F108 20 mg/mL | NaDOC 2 mg/mL | Cholesterol 10 mg/mL | F68 20 mg/mL |
| O | All components of N | PVP 20 mg/mL | | | |
| P | DSPC 10 mg/mL | PVP 20 mg/mL | Gelatin 6 mg/mL | | |
| Q | DSPC 10 mg/mL | F108 20 mg/mL | Gelatin 6 mg/mL | | |
| R | All components of Q | F68 20 mg/mL | Cholesterol 10 mg/mL | | |
| S | DSPC 20 mg/mL | F108 20 mg/mL | Cholesterol 10 mg/mL | Gelatin 6 mg/mL | |
| T | DSPC 20 mg/mL | Cholesterol 10 mg/mL | Gelatin 6 mg/mL | NaDOC 2 mg/mL | PVP 20 mg/mL |
| U | DSPC 20 mg/mL | Gelatin 3 mg/mL | Cholesterol 10 mg/mL | | |
| V | DSPC 1 mg/mL | F68 10 mg/mL | Cholesterol 5 mg/mL | | |
| W | DSPC 5 mg/mL | F68 10 mg/mL | Cholesterol 5 mg/mL | | |
| X | DSPC 5 mg/mL | F68 10 mg/mL | Cholesterol 10 mg/mL | | |
| Y | DSPC 5 mg/mL | F68 5 mg/mL | Cholesterol 5 mg/mL | | |
| Z | DSPC 10 mg/mL | Brij 5.9 mg/mL | | | |
| AA | DSPC 5 mg/mL | Cholesterol 5 mg/mL | | | |
| BB | DSPC 10 mg/mL | Brij 5 mg/mL | Cholesterol 5 mg/mL | | |
| CC | DSPC 10 mg/mL | Cholesterol 10 mg/mL | | | |
| DD | DSPC 10 mg/mL | Poloxamer 188 10 mg/mL | | | |

In a preferred embodiment, the microbubbles contain DSPC in combination with cholesterol, Pluronic F68 (Poloxamer 188), and/or PVP. In these embodiments, DSPC is present in a concentration ranging from 6.3 wt % and 67.7 wt %. Cholesterol can present in a concentration ranging from 1-50 mass %.

B. Carrier

The oxygen-containing microbubbles are suspended in a suitable pharmaceutically acceptable carrier. The carrier should be generally isotonic with blood. Suitable carriers include, but are not limited to, Plasma-Lyte A, normal saline, physiological saline or water containing one or more dissolved solutes, such as salts or sugars, which do not substantially interfere with the formation and/or stability of the microbubbles. The carrier may be a synthetic colloid, such as 6% hetastarch (ethoxylated amylopectin) combined with a physiologically balanced crystalloid carrier that is similar to the plasma electrolyte balance (Hextend®, BioTime, Inc.), or hemoglobin-based oxygen carrier (HBOC), e.g. PolyHeme® (Northfield Laboratories, Evanston, Ill.), Hemopure® (HBOC-201) (Biopure Corp., Cambridge, Mass.), or HemoLink™ (Hb-raffimer) (Hemosol Inc, Toronto, Canada). In this embodiment, after the microbubbles release the oxygen in vivo, they leave behind the lipid envelope, which exhibits strong oncotic pressure, and carrier, which serves as a volume expander.

C. Storage Conditions

LOMs can be stored in a variety of containers in a variety of conditions. For example, LOMs can be stored in a freezer, a refrigerator, at room temperature or under heated conditions. In one embodiment, LOMs can be stored frozen at −20° C. and thawed quickly by running warm tap water over the syringe, or by heating in a microwave.

IV. Uses for the Oxygen-Containing Microbubbles

The oxygen-containing microbubbles described herein can be administered to a patient in need thereof to quickly increase blood oxygen levels. In the preferred embodiment, the oxygen content of the LOM formulation that is administered to a patient ranges from about 60% to about 80% (vol).

One mechanism by which viscosity of the LOM suspension may be lowered prior to injection is by mechanical pre-shearing. For example, an in-line helical static mixer may be incorporated within an infusion syringe to pre-shear the suspension just prior to infusion.

A. Patients to be Treated

Examples of patient populations that may be treated with the oxygen-containing microbubbles include, but are not limited to, patients with severe cyanotic congenital heart disease, cardiac arrest, hypoxemia, carbon monoxide poisoning, necrotizing enterocolitis, and/or ischemic colitis.

For example, an effective amount of an oxygen-containing microbubble formulation could be administered to a patient to bridge the time from onset of severe hypoxemia (refractory to traditional maneuvers) and successful placement of a tracheal tube. Administration of LOMs would allow patients with anatomically abnormal airways or with less-skilled medical providers to be safely transported to an appropriate facility, or for multiple attempts at intubation to take place safely. In some embodiments, a bolus of LOMs just at the onset of asphyxia may provide basal oxygen consumption to the brain and to the myocardium and prevent loss of circulation and organ injury. In the case of cardiac arrest, LOMs can be administered to a patient to supplement the current standard of care as set forth by the American Heart Association, which includes CPR, inotropic agents and defibrillation. In other embodiments, continuous infusions of LOMs can be administered to a patient to create circulating arterial pockets of oxygen, providing a new way to supplement oxygen delivery and therefore new approaches to shock states.

Patients with severe cyanotic congenital heart disease (e.g. unrepaired d-transposition of great arteries with poor mixing) can be stabilized by administering an effective amount of the LOMs to raise the oxygen content of the systemic venous return, and thereby prevent pre-operative morbidity prior to definitive care (such as balloon atrial septostomy). In one embodiment, the LOM formulation can be applied topically to the peritoneum to enhance oxygen delivery to ischemic bowel (as in the case of ischemic colitis or neonates with necrotizing enterocolitis).

In another embodiment, the LOM formulation may be applied topically at the site of a wound in an effective amount to enhance wound healing. The LOM formulation can be applied topically on a continuous basis to infected wounds, as is the case with necrotizing fasciitis, in which the creation of hyperoxic wound conditions is known to decrease mortality and amputation from the disease. The conditions created by the LOM suspension are likely to be unsuitable for bacterial growth, especially so in the case of anaerobic bacterial organisms. This therapy would complement traditional antimicrobial agents (antibiotics) by providing a new mechanism for bacterial killing which would not be amenable to traditional mechanisms for bacterial resistance.

In yet another embodiment, the LOM formulation may be administered to an infant, typically a premature newborn infant, with acute necrotizing enterocolitis (NEC). Optionally, the LOM formulation may be administered to infants at risk of NEC as a prophylactic treatment, in an effective amount to prevent NEC. NEC is characterized as an acute onset of intestinal inflammatory necrosis which manifests as abdominal distension, gastrointestinal bleeding, and pneumatosis intestinalis. NEC is a multifactorial disease process, a major component of which is regional tissue hypoxia due to microvascular obstruction, dysregulation and immaturity. The LOM formulation may be topically applied to the patient's peritoneal cavity or the intestinal lumen in an effective amount to provide sufficient oxygenation to the small intestine. Administration of the LOM formulation is preferably effective to improve mesenteric oxygen delivery during acute NEC.

B. Methods of Administration of the LOM Formulations

The LOM formulations are typically administered by a suitable method to provide intravascular oxygen delivery. In some embodiments the formulation is administered as an intravenous infusion or a bolus; in others it is administered by intraosseous infusion or a bolus; and in yet others the formulation is administered topically to the tissue in need of treatment.

For example, the LOM formulation may be applied to the subdural space, for example, to deliver oxygen to the brain in case of embolic stroke.

Alternatively, the LOM formulation may be administered as an intravenous or intraosseous infusion to a patient with severe hypoxemia to raise oxyhemoglobin saturation and increase arterial blood gas values, preferably within 1 minute, more preferably within 30 seconds of beginning the infusion. As shown in Example 7, oxyhemoglobin saturation and oxygen tension can be acutely raised by intravenous or intraosseous infusion of LOMs.

Oxygenated microbubbles can be administered to patients with severe carbon monoxide poisoning to treat the patients in a more rapid and practical way than hyperbaric oxygen therapy.

Small boluses of oxygen into the bloodstream can create an immediate change in oxyhemoglobin saturation (e.g. from 95% to 100%), and thereby non-invasively quantify cardiac output based on the time delay from injection of the drug to a change in the pulse oximeter.

Patients can be treated with an effective amount of LOMs to maintain a survivable oxygen saturation and/or a stable blood pressure. Further, administering the LOMs to a patient in need of oxygen may be effective to produce less metabolic acidosis, increase production of carbon dioxide and/or lower incidence of cardiac arrest relative to controls, i.e. receiving standard of care without LOM infusions.

In another embodiment, LOM formulation may be administered to a patient who is undergoing CPR. As shown in Example 6, continuous chest compression only (CCC) CPR is, over time, associated with a decline in cerebral oxygen delivery and severe hypoxemia, which accounts for the brain injury which results. CCC CPR, when prolonged, also results in progressive endothelial failure, which results in lack of a diastolic blood pressure (which is the primary determinant of coronary perfusion pressure, and the likelihood of return of spontaneous circulation). CPR may therefore be more effective if LOMs are administered to the patient, especially in the setting of a lack of an advanced airway, such as a tracheal tube. Preferably the LOM formulation is administered simultaneously while a patient is undergoing CPR.

In other embodiments, the oxygen-containing microbubbles can be used to oxygenate products such as donated blood products and radiographic contrast agents (as used for angiograms). Donated blood products (typically taken from a donor's vein) could be oxygenated by admixture of a small volume of oxygenated microbubbles, which may improve the health of stored blood and prolong its shelf life. In another embodiment, LOMs may be used to oxygenate contrast agents used for coronary angiography, in an effective amount to decrease the risk of life-threatening arrhythmias during contrast administration.

The oxygen-containing microbubbles described herein can also be filled with other gases, such as those used for suspended animation, permitting selective application of the technique to selected organs. They may also be filled with inhalational anesthetics to provide a new class of sedative and anti-epileptic medications.

LOMs can be used to control the oxygen tension within microenvironments, which may be useful in cardiac tissue engineering or to direct stem cell differentiation.

EXAMPLES

Example 1: Stable LOM Suspensions Made by High Shear Homogenization

A study was conducted to make stable LOM suspensions with a target microbubble size that contains approximately 90 vol % oxygen gas. Microbubbles were made following different protocols, in an attempt to increase their volume (height) stability.

Materials and Methods

Hydrating Lipids.

Each combination of lipid excipients (see Table 1) were hydrated in 1 liter of Plasma-Lyte A (Baxter Corporation, Deerfield, Ill.) at room temperature. Base lipids and stabilizing agents were provided as a powder, and were mixed with the aqueous phase using a large stationary mixer (Silverson L5MA, Silverson Machines, Incorporated, East Longmeadow, Mass.), fitted with a medium mesh emulsor screen. Chemical excipients were sequentially added to the aqueous phase and mixed at 5,000 RPM for 5 minutes. This resulted in clear fluid with no residual particulate matter for nearly all lipid combinations. These hydrated lipids were stored at 4° C. used for LOM manufacture. The concentration of the lipid components within the solution, particularly that of DSPC, affects the final concentrated volume gas fraction of LOMs within the suspension following the homogenization step. For example, 10-20 grams/L of DSPC can result in gas fractions of up to 90 vol % without the need for centrifugation, whereas 5 grams/L of DSPC mandates the need to concentrate the LOMs by centrifugation.

LOM Manufacture.

To begin the manufacturing process, hydrated lipids were placed into the customized glass container (Specialty Glass, Incorporated, Rosharon, Tex.) shown in FIG. 1B.

Introduction of Precursor Components into the Homogenizer

Compressed oxygen gas (Oxygen, Compressed USP, Airgas East, Incorporated, Salem, N.H.) was pumped through a flowmeter (AmVex Corporation, Richmond Hill, Ontario, Canada) at 60 mL/minute, and then into a custom T-piece. The oxygen gas and hydrated lipids mixed within the customized T piece and then entered an inline, closed homogenizer (Silverson Verso, Silverson Machines, Inc.). The two phases were mixed at high shear rates (5,000-8,000 RPM). As the oxygen gas and hydrated lipids pass through the T-piece, they enter core of the homogenizer (FIG. 1D).

Within the homogenizer, gas and hydrated lipids passed through two ultra-fine mesh emulsor screens (FIG. 1D) and were sheared by the rotor stator. The rotor and screens are designed to allow an ultrafine distance between the rotor and screen, creating high shear conditions. These conditions impose high energy to the lipid-gas interface, creating size-limited, self-assembling microbubbles. These microbubbles must pass through the emulsor screens to exit the device, creating an additional size-limiting step. Although the pores in the screens used in this experiment were approximately 500 microns in size, emulsor screens can be made with any mesh filter, and may have smaller pores, such as in a 20 or 10 micron mesh screen. The microbubble suspension then exited the homogenizer from the side port and passed through a heat exchanger (BIOtherm, Medtronic, Minneapolis, Minn.) where it was cooled to 4° C. This stabilized the lipid envelope and dissipated the heat created in the manufacturing process. Gas-filled microparticles were then returned to the glass container in FIG. 1B, where they were recycled through the manufacturing process.

When the process is continued for 30 minutes with no additional modifications, the resulting suspension can be concentrated to 70 vol % prior to centrifugation. In an alternate embodiment, the storage container is maintained above, such as approximately 4 feet above, the homogenizer, and the roller pump is not used to feed the homogenizer. When this setup is run for 40 minutes, a 90 vol % oxygen gas can be created without the use of centrifugation as a concentrating step.

Concentrating LOM Suspension.

LOMs manufactured as described above were concentrated as follows. Hydrated lipids were run through the system described above for 15 minutes. A roller pump was set at 1.5 liters per minute and oxygen gas was fed at 60 mL/minute continuously. This resulted in approximately 900 mL of oxygen gas mixing with 1,000 mL of hydrated lipids in the aqueous phase, resulting in an approximately 50 volume % suspension. The recycling process was stopped at this point, and the resulting suspension was withdrawn into 140 mL syringes which had been modified for this process. Syringes were capped and then centrifuged at 1,000 RPM for 10 minutes. This resulted in a three phase separation within each syringe. (a) At the lowest centrifugal force was approximately 5 mL of free oxygen gas. This may be gas that was trapped within the diluent or carrier, or more likely, gas released from oversized, unstable particles. Larger particles have a higher surface tension and are therefore more likely to become unstable in storage or under weak centrifugal forces. In this way, centrifugation may serve as a purification step in removing large microbubbles from the suspension. (b) Within the center of each syringe was a large section of concentrated, bright white microbubbles (data not shown). These particles were large enough to be somewhat buoyant above the aqueous phase below them; in contrast very small particles (e.g. nanobubbles) which are minimally buoyant contain very little gas relative to the volume of the lipid shell and are therefore believed to be inefficient gas carriers (Cavalli, et al., *Int. J. Phar.*, 381:160-165 (2009)). This portion of microbubbles was collected into larger syringes for storage and in vitro characterization. (c) At the highest centrifugal force (bottom of the syringe) were hydrated lipids and the majority of the aqueous phase (data not shown) (Feshitan, et al., *J Colloid Interface Sci.*, 329:316-324 (2009)). This fluid was collected for re-use or discarded.

An alternative method to concentrate the gas phase was to continue to recycle the hydrate lipids through the homogenizer. In one iteration, this process was continued for 30 minutes using the roller pump to continue to pump the gas phase through the homogenizer. As the gas phase increased above 50-60 volume %, the suspension became increasingly viscous and difficult to pump. As a result, the roller pump trapped increasing volumes of oxygen gas, and encapsulation efficiency decreased. Pressurizing the chamber permitted the viscous LOM suspension in the chamber to be pushed out of the chamber outlet and into the homogenizer.

LOM Formulation Stability Testing.

Eight lipid and biocompatible chemicals were selected for testing as suitable LOM excipients. After pilot testing using empiric combinations of lipids, these excipients were used to design a stability testing experiment using design of experiment software (JMP 9, Version 9.0.0, SAS Institute, Inc., Cary, N.C.). Variables included mass percentage of 1,2-distearoyl-sn-glycero-3-phosphocholine (DSPC), polyethylene glycol-block-poly(propylene glycol)-block-poly(ethylene glycol), Poly(propylene glycol)-block-poly(ethylene) glycol (SYNPERONIC® F108), Polyethylene-Polypropylene Glycol block co-polymer (Pluronic F68) (Singh-Joy, *Int. J. Toxicol.*, 27(Suppl 2):98-128 (2008), cholesterol, gelatin, sodium deoxycholate, polyvinylpyrrolidone (PVP), and polyoxyethylene (100) stearyl ether (BRIJ 100). Other excipients such as lecithin, soybean oil, coconut oil, and glycerol were initially screened, but not selected for this study as they did not appear to contribute substantially to particle stability.

Limits were set upon the concentrations of each of the components, such that no one constituent could constitute more than 5 mass percent of the solution, and the concentrations of the lipids were minimized as much as possible. Outputs included (a) ability to form intact LOMs, (b) particle size (fraction exceeding 10 microns in diameter) following manufacture, (c) percentage of original particles remaining at 2 weeks at 4° C. Although other outputs were measured, these three outputs were considered to be the most representative of the desired outcome, which was to manufacture a size-limited suspension of LOMs. Combinations of excipients tested are listed in Table 1.

1 liter of hydrated lipids were formed for each combination for the stability analysis. LOMs were manufactured according to the methods described above. This created a variable volume of concentrated LOMs (in part depending upon encapsulation efficiency). Following manufacture, combinations were allowed to stand for 24 hours at 4° C. Thereafter, candidate LOMs were distributed into glass tubes (Pyrex 9825-16X culture tube, Corning Incorporated, Corning, N.Y.) for subsequent observation. 2 mL of water were added to the base of each test tube to allow for mixing of the gas phase when large bubbles became trapped within the suspension.

Stability Measurements.

For each combination that had sufficient particles remaining at 24 hours (n=14), three tubes were observed at 4° C., three tubes at room temperature, and two tubes under 'backpack conditions' (i.e. continuous oscillation at 30 oscillations per minute, 100% humidity, 30° C.; Precision reciprocal shaking water bath, Thermo Scientific, Marietta, Ohio), and one tube at −20° C. Suspensions were observed weekly and the height of remaining concentrated microbubble suspension was visually inspected and measured.

Particle Size Distribution.

Particle size distribution of samples stored at 4° C. was determined by sampling twice per month using light obscuration (Accusizer 780A, NICOMP Particle Sizing Systems, Santa Barbara, Calif.) (Swanson, et al., *Langmuir*, 26:15726-15729 (2010)). 10-μL samples of LOM suspension were directed into a 30-mL flask under low convective motion. Raw particle size distribution data was analyzed by NICOMP Particle Sizing Systems, software version 1.71, which outputs mean particle diameter and number percentage of particles exceeding 10 microns in diameter for each sample analyzed by linear regression analysis.

Viscosity.

The viscosity profiles of three representative combinations was determined, selected based on their stability profiles. Two mL aliquots LOM suspensions at 90 volume percent (n=3 per group) were studied using a 40 mm parallel plate geometry (AR 2000ex, TA Instruments, New Castle, Del.). The steady state flow viscosity was measured as stress was varied from 0.1 to 10,000 μn-m. Temperature was maintained at 25° C. No pre-conditioning step was used.

Because the shear rate of blood within the circulation is generally accepted to be a shear rate 200 seconds$^{-1}$, viscosity at this shear rate was determined from the flow sweep (Jonas, et al., *Cardiopulmonary bypass in neonates, infants and young children.* (Butterworth-Heinemann, Oxford; Boston, 1994), pp. xii, 312 p.)). Results were compared between groups by 1-way ANOVA with Dunn's multiple comparison post-test.

Oxygen Transfer Efficiency.

In order to determine the completeness with which the candidate LOM formulations transfer oxygen to hemoglobin, a simple test of oxygen transfer was conducted. Donated human red blood cells were deoxygenated by exposure to a nitrogen gas headspace while under continuous stirring motion and warmed to 30° C. Oxygen content of a 10 mL aliquot was tested by arterial blood gas and co-oximetry (ABL80 FLEX CO-OX, Radiometer America, Incorporated, West Lake, Ohio). Aliquots of 50 vol % LOMs were added to test tubes, and the volumes of oxygen gas added to each test tube varied. Following mixing by gentle rocking for 30 seconds, oxygen content of the sample was again calculated. The change in oxygen content was plotted against the volume of oxygen instilled in LOMs and analyzed by linear regression.

Results

Overall, the manufacturing process described in this example was extremely successful. The use of high shear homogenization improved scalability, improved the ability to concentrate LOMs during the manufacturing process and improved sterilizability. Using this process, 1 liter of 90 volume % LOMs was prepared in 3-4 hours, as compared to 2-3 days of two technicians' time, if sonication were used.

Stability.

Fourteen of the excipient combinations shown in Table 1 efficiently encapsulated oxygen using the methods described above and were further observed for a three month period. With reference to Table 1, these were combinations A, B, C, D, E, I, K, L, P, Z, AA, BB, CC and DD. There was a composition-dependent disparity in survivability among combinations. For clarity, five representative combinations are depicted in FIG. 2A-2D. At 4° C., several of the samples suffered an initial decline in volume (likely due to microparticle breakdown and release of free gas), with a subsequent period of stability over the ensuing 3 month observation period. Combination C did not lose substantial volume over the 3 month period of observation. At room temperature, only combination C maintained>75% of its original volume during the observation period. Under backpack conditions (100% humidity, constant motion, 30° C.), combination C maintained>80% of its original volume for three months. While the remaining suspensions lost most or all of their volume by 1 month, combination C maintained a clear, white suspension containing microbubbles under backpack conditions, which include heat, humidity and constant motion. At −20° C., the suspensions were largely frozen, and none of them appeared to lose volume.

Size Distribution.

Figure 3A:
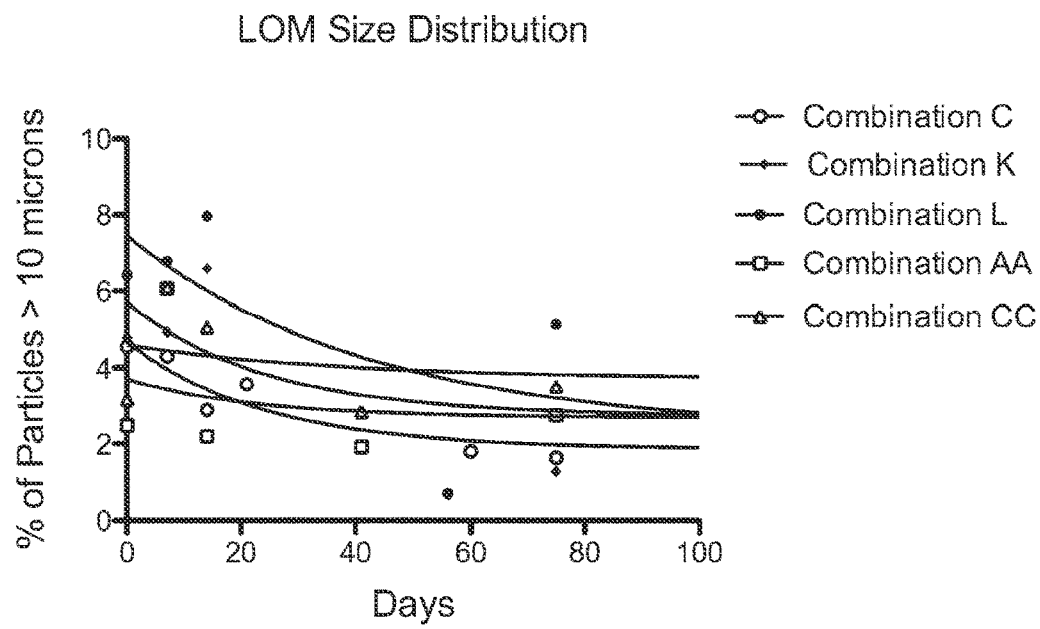
FIG. 3A is a graph showing particle size distribution over time for five representative combinations of LOM excipients (C, K, L, AA, CC in Table 1).

All lipid combinations demonstrated a generally low percentage of large particles exceeding 10 microns in diameter. Because suspensions containing up to 10 number % of LOMs in excess of 10 microns diameter have been utilized with acceptable hemodynamic effects at high infusion rates (unpublished results), 10% above 10 microns was used as a standard cutoff for particle size. As shown in FIG. 3A, combination C in particular exhibited a small number of particles exceeding 10 microns in diameter, and this number did not increase over the 3 month observation period.

Viscosity.

The viscosity of LOMs at the shear rate of the human circulation was characterized for three lipid combinations and for donated human erythrocytes (hematocrit ~60%). The viscosity of combinations C (0.0766±0.006 Pa*s) and K (0.3275±0.0167 Pa*s) were statistically similar to that of blood (0.0188±0.001 Pa*s), while that of combination L (0.527±0.115 Pa*s) was higher than the viscosity of blood (*, p<0.05). No detrimental hemodynamic effects were observed when combination C was injected into animals during other in vivo studies.

Oxygen Transfer.

Figure 3B:
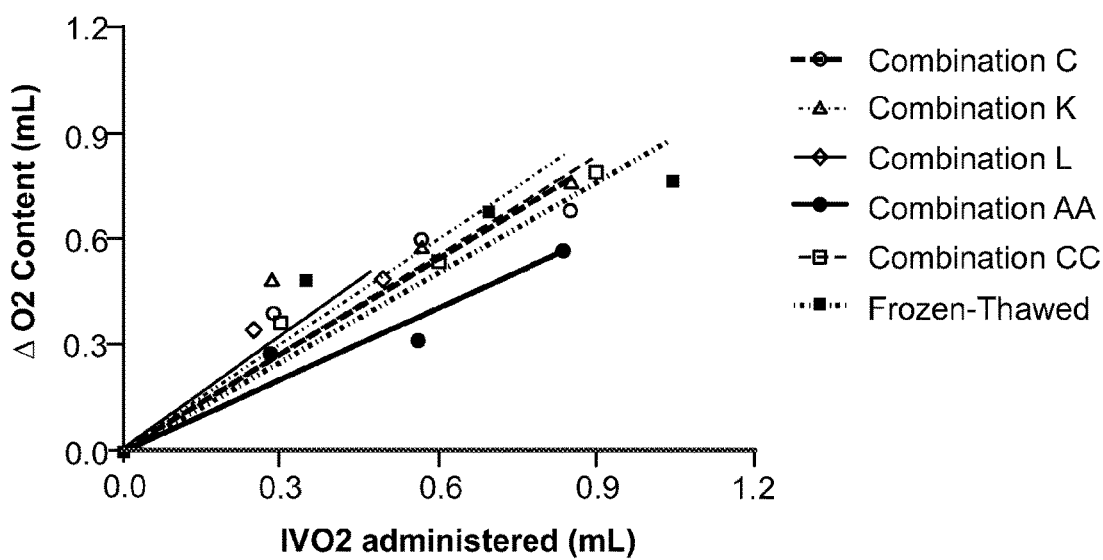
FIG. 3B is a graph showing oxygen transfer to blood for Combinations C, K, L, AA, CC, as well as for Combination C after it had been frozen for 1 week at −20° C. and subsequently thawed.

All five combinations (C, K, L, AA and CC) demonstrated a nearly-linear dose response with a slope approaching 1 (see FIG. 3B), indicating that nearly 100% of the oxygen gas contained within LOMs transferred from the gas core to blood.

Example 2: LOM Suspension Viscosity as a Function of Microbubble Volume Percentage Oxygen-containing microbubbles were made from 1,2-distearoyl-sn-glycero-3-phosphocholine (DSPC) and polyoxyethylene (100) stearyl ether (BRIJ 100).

Briefly, DSPC (10 mg/mL) and BRIJ 100 (10 mol %) were hydrated in 0.9% sodium chloride. LOMs were manufactured as described above using shear homogenization and centrifugation. The resulting suspension was diluted to contain LOMs of 65 to 90 volume %.

Rheometry Measurements.

Two mL aliquots of donated human packed red blood cells and microbubble suspensions of DSPC and 10 mol % BRIJ 100 at 65, 80 and 90% volume percent by weight (n=8 per group) were studied using a Rheometer with 40 mm parallel plate geometry (AR 2000ex, TA Instruments, New Castle, Del.) to measure their viscosities. Stress was varied from 0.1 to 10,000 µN-m. Temperature was maintained at 25° C. by Peltier plate. No conditioning step was used. Yield stress was calculated as the onset point of the viscosity-shear stress relationship (TRIOS Software version 2.0, TA Instruments, New Castle, Del.). Zero- and infinite-stress viscosity were calculated using the Ellis Flow Model (TRIOS Software version 2.0, TA Instruments, New Castle, Del.). Viscosity at a shear rate of 2,000/second was gathered from the flow sweep.

Effect of volume percentage on yield stress and on viscosity at a shear rate of 2,000/sec was analyzed by Kruskal-Wallis test with Dunn's multiple comparison post-test. Groups were compared by 2-way ANOVA and Bonferroni post-test to account for repeated measures, and a Dunn's multiple comparison post-test.

Figure 4A:
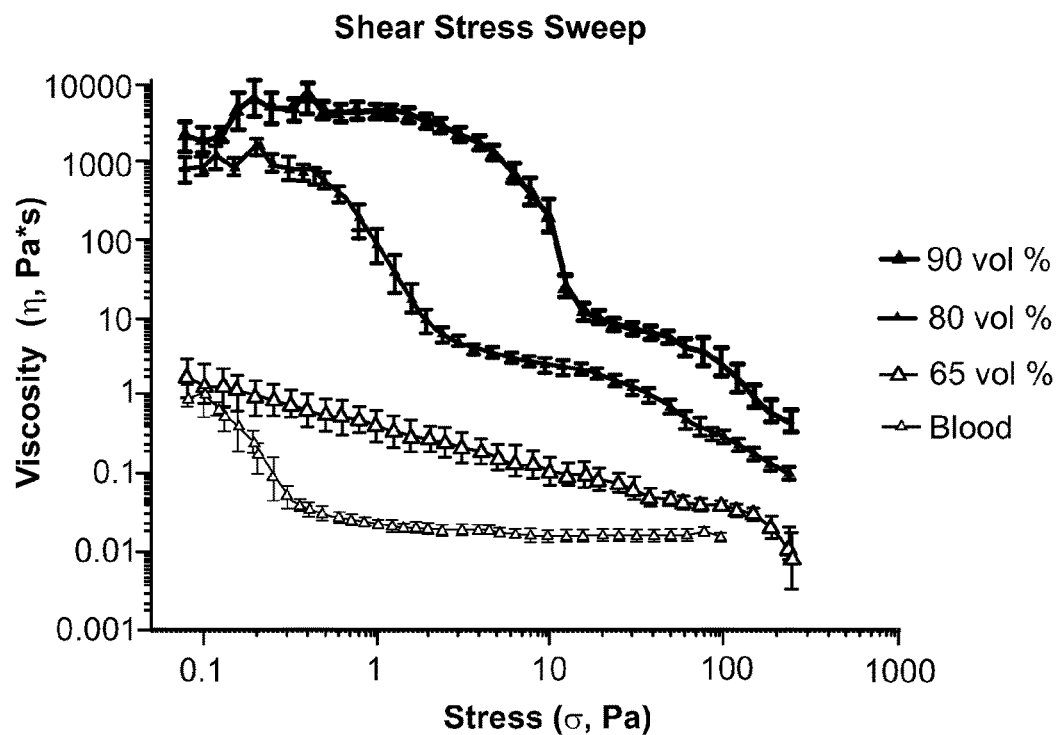
FIG. 4A is a graph showing suspension viscosity as a function of microbubble gas fraction.

The data showing viscosity as a function of microbubble volume percentage at 65, 80 and 90% volume percent by weight (n=8 per group) are provided in FIG. 4A.

Figure 4B:
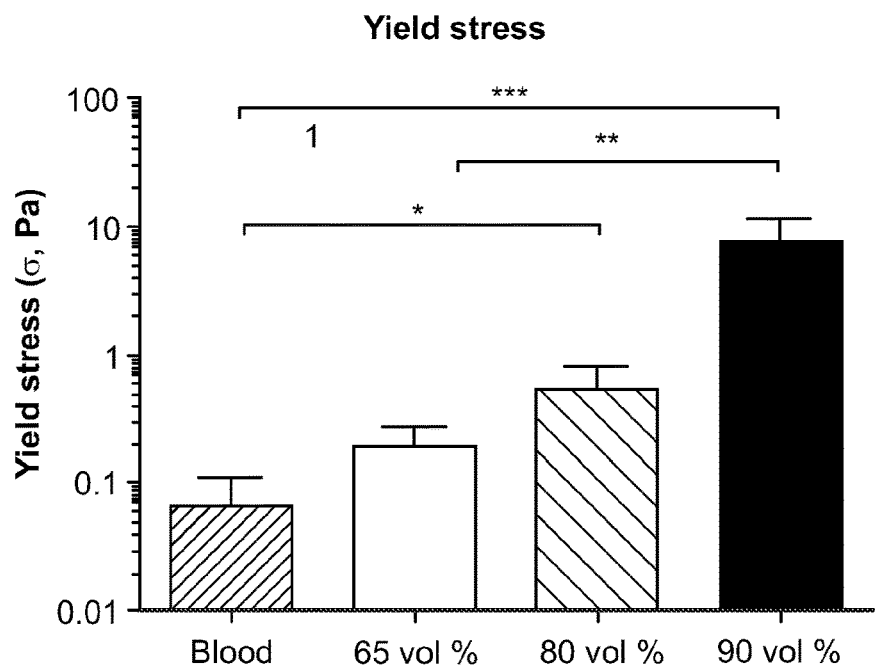
FIG. 4B is a graph showing yield stress as a function of microbubble volume percentage.
Figure 4C:
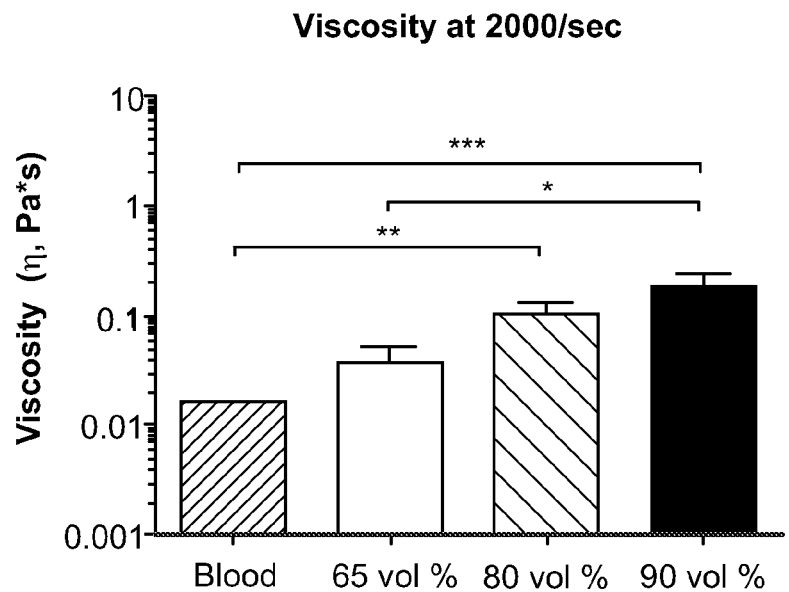
FIG. 4C is a graph showing viscosity at a shear rate of 2000/sec, as a function of microbubble volume percentage.
Figure 4D:
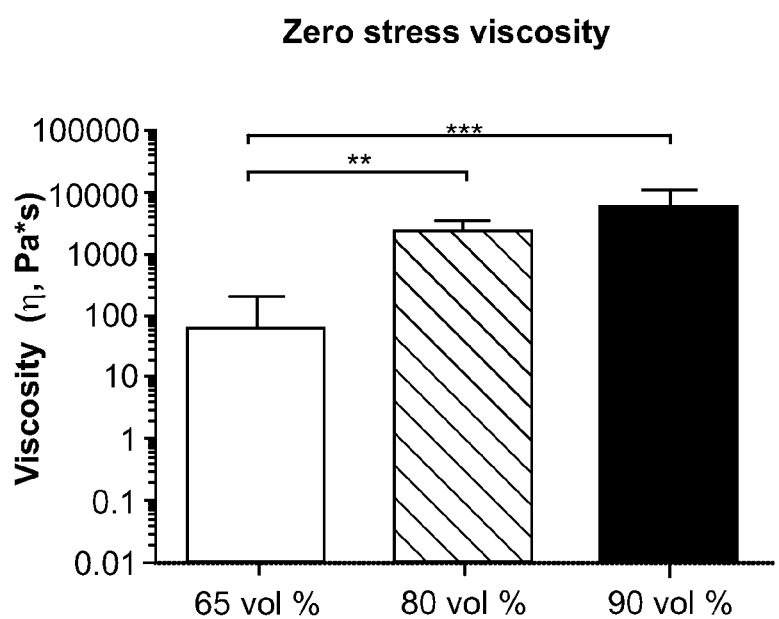
FIG. 4D is a bar graph showing viscosity as a function of microbubble vol %, at zero stress.

At low shear, viscosity of 65 volume % microbubbles and human blood was similar, approximately $10^3$ lower than that of 80 and 90 volume %. This difference became significant (P<0.05) at stresses above 2.5 Pa (2-way ANOVA with Bonferroni post-test. At shear volume equivalent to infusion through a catheter, 65 volume % microbubbles exhibited a viscosity similar to human blood. Yield stress increased with increases in volume percentage (FIG. 4B). Yield stress at 90 volume % was significantly higher than at 65 volume %. Relative to that of blood, yield stress of LOM suspensions was significantly higher at 90 volume % and at 80 volume % as calculated by Kruskal-Wallis test with Dunn's multiple comparison post-test. There was no significant difference in yield stress between blood and 65 volume % LOM. Column height represents mean, error bars represent 95% confidence interval. Zero stress viscosity was significantly higher for 80 volume % and 90 volume % relative to 65 volume % as calculated by Kruskal-Wallis test with Dunn's multiple comparison post-test (FIG. 4D).

A shear rate of 2,000 $\sec^{-1}$ approximates the theoretical shear of a fluid being injected at 100 mL/minute through a 14 gauge (2.1 mm diameter) angiocatheter tip as follows:

$$\text{Shear rate} = (4 \times \text{flow rate})/(\pi \times \text{radius}^3) =$$
$$(4 \times 1.66 \text{ cm}^3/\text{sec})/(\pi \times (0.105 \text{ cm})^3) \approx 2,000/\text{sec}$$

(Bernard, et al. *Am J Respir Crit Care Med*, 149:818-824 (1994)).

At a shear rate of 2,000 $\sec^{-1}$, viscosity was higher at 90 volume % LOM and at 80 volume % LOM relative to the viscosity of blood by Kruskal-Wallis test with Dunn's multiple comparison post-test. Viscosity of 65 vol % LOM was not significantly higher than the viscosity of blood. FIG. 4C, n=8 samples per group.

Figure 4E:
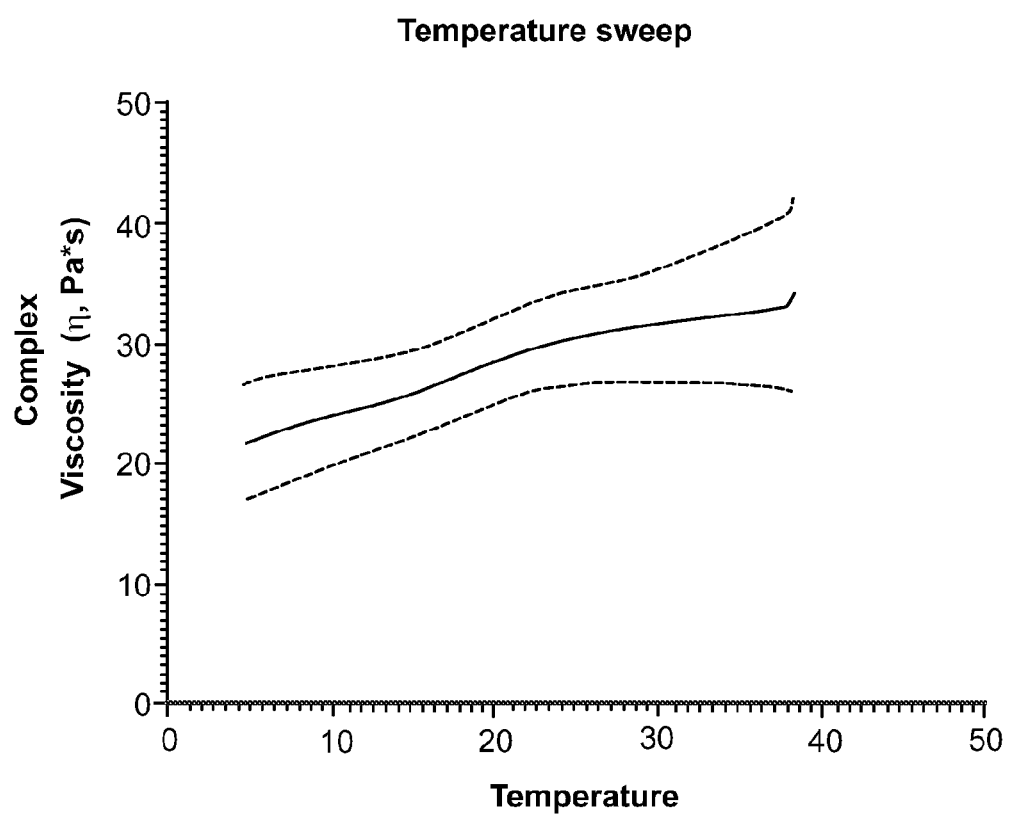
FIG. 4E is a graph showing complex viscosity of a 90 volume % suspension as a function of temperature (n=8 samples, solid line represents mean, dotted lines represent 95% confidence interval (CI)).

Infinite stress viscosity was significantly higher for 90 volume % LOMs when compared with blood or 65 volume % LOMs. There were no other significant differences between any groups shown by Kruskall-Wallis test (data not shown). Complex viscosity of a 90 volume % suspension increased linearly with temperature (P<0.00, linear regression) within the range tested. (FIG. 4E).

Example 3: In Vitro and In Vivo Oxygen Transfer from LOM

In Vitro Oxygen Transfer.

10 mL aliquots of donated human packed red blood cells were distributed into 15 mL glass test tubes. Test tubes were filled with 2 mL of human blood and mixed with different volumes of LOM, prepared according to the methods described herein. Baseline hemoglobin, oxyhemoglobin saturation by co-oximetry and oxygen tension were quantified (Radiometer ABL 80 Co-Ox Flex, Radiometer America, Denmark) for calculation of oxygen content as follows:

$CaO_2$=1.34 mL oxygen/dL blood×hemoglobin concentration×oxyhemoglobin saturation+0.0031× dissolved oxygen tension.

Varying volumes of LOMs were added to each test tube. The volume of oxygen gas added to each test tube was quantified by weight differential in a 3 mL syringe containing a known volume of suspension. Blood and LOMs were mixed by inverting the test tube three times, and oxygen content quantified again. Change in oxygen content was calculated for each test tube and compared between doses by linear regression.

Figure 5A:
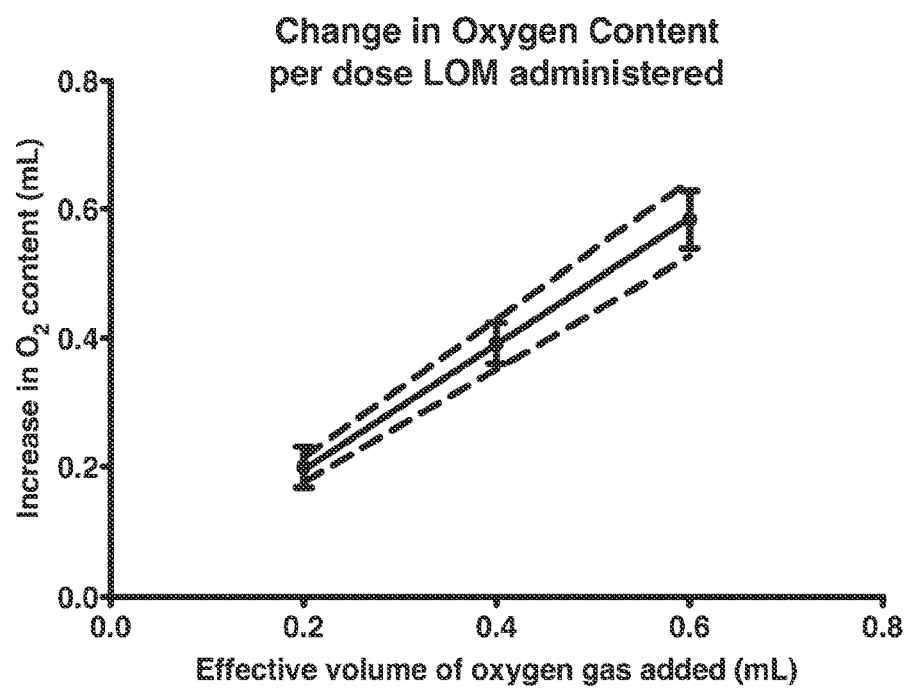
FIG. 5A shows change in oxygen content per dose of LOM administered (70 volume % LOMs used). n=5 samples per group. Slope of linear regression line is 0.9761 (95% CI, 0.8790 to 1.073). Error=95% CI, solid line=linear regression line, dotted line=95% CI of linear regression. r2=0.9286, slope is non-zero (p<0.0001).

Results:

Oxygen content increased linearly with addition of increasing volumes of LOMs (70 volume % LOMs used). When mixed with blood in a test tube, LOMs transfer oxygen to desaturated erythrocytes with near complete efficiency (FIG. 5A).

Figure 5B:
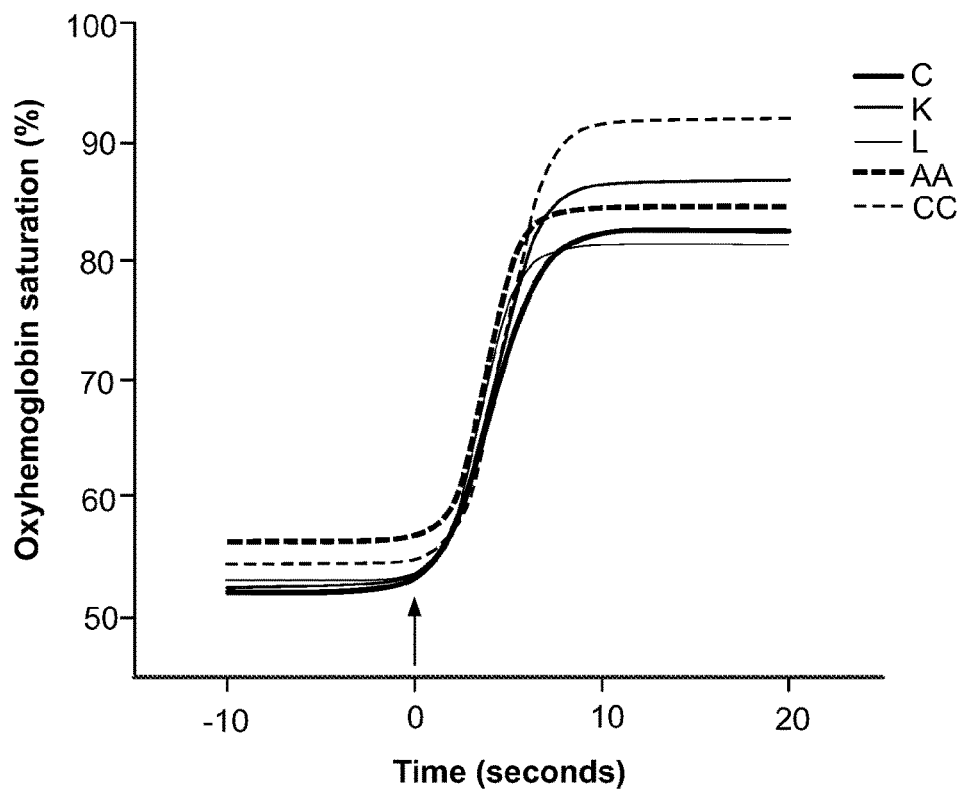
FIG. 5B shows change in oxyhemoglobin saturations measured in real-time during injection of 50 volume LOMs into a beaker containing 100 mL of human blood under continuous motion.
Figure 5C:
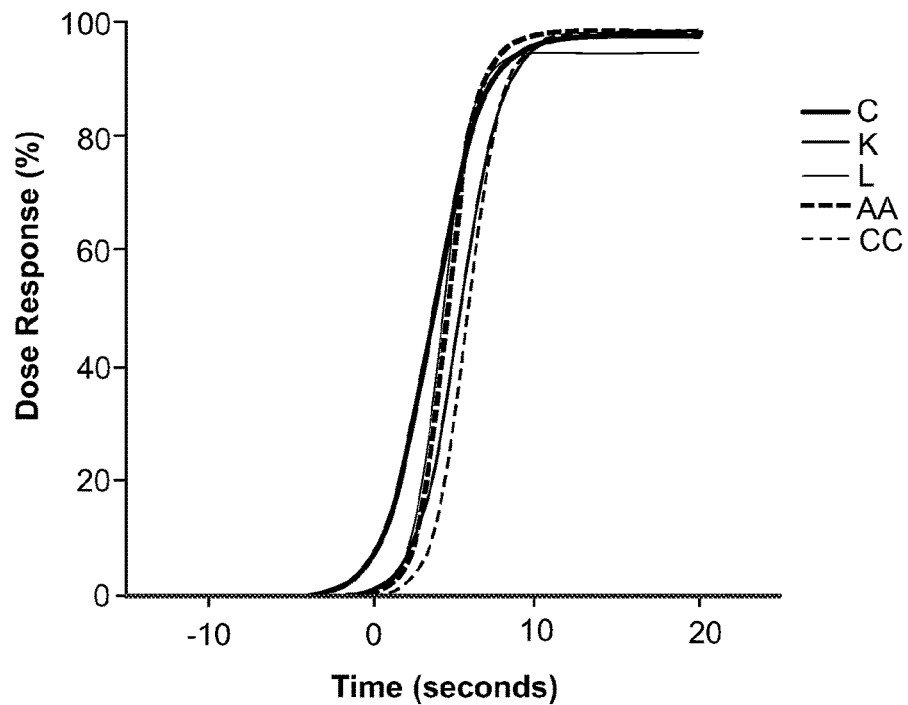
FIG. 5C shows the percentage of oxygen release (dose response) of 50 volume % suspensions of varying compositions to desaturated human blood.

To test release kinetics, 100 mL of human blood was circulated within a beaker (see FIG. 5B: initial $SaO_2$ 53%, Hgb 10 g/dL). 13 mL aliquots of oxygen contained within 50 vol % LOMs from combinations C, K, L, AA and CC (n=4 replicates per combination) were injected into the beaker, and the change in oxyhemoglobin saturation was monitored continuously using a co-oximeter (Cobe Instruments). Oxygen saturations rose rapidly with injection and plateaued within 5 seconds of the addition of LOMs from any combination to the blood. The percentage of oxygen contained within the LOMs which transferred to blood as a function of time is plotted in FIG. 5C, and suggests that oxygen transfer is efficient and complete from any of these lipid combinations within 10 seconds.

Figure 5D:
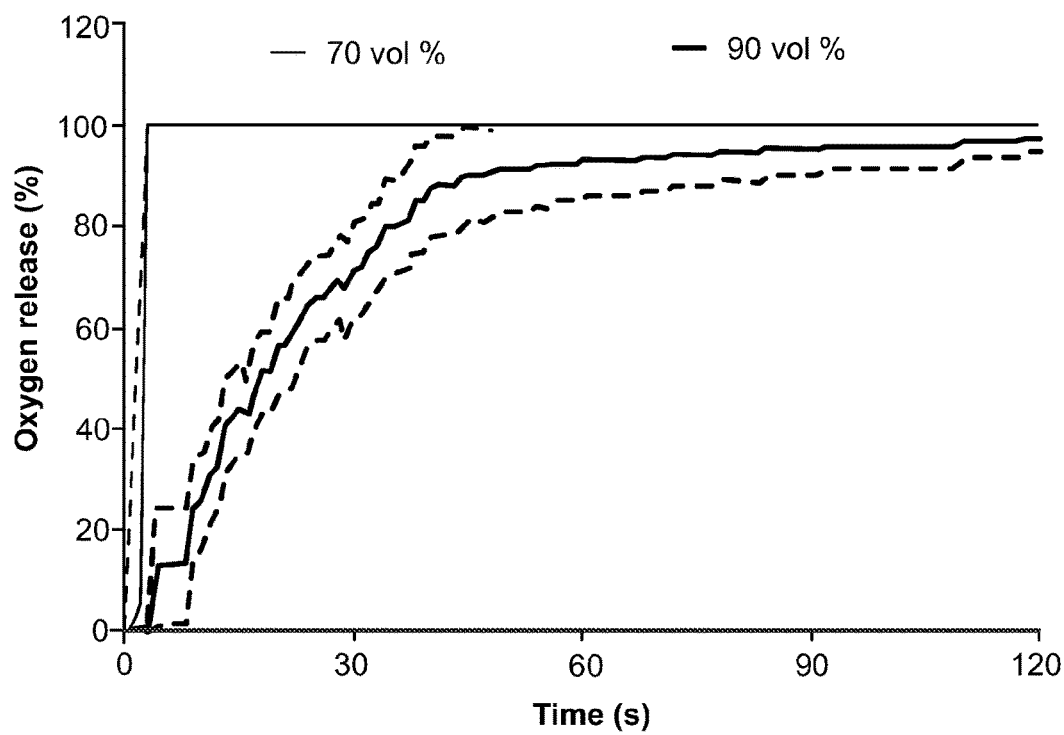
FIG. 5D depicts the rate of oxygen release to human blood as a function of vol % for 70- and 90 vol % LOM suspensions.

Finally, the oxygen release kinetics from LOMs of 70 versus 90 vol % gas fractions was compared in a similar setup. 100 mL aliquots of human blood were desaturated using nitrogen gas, and heated to 37° C. on a stirplate. 9 mL of oxygen gas contained within either 70 or 90 volume % LOMs (composed of BRIJ and DSPC) were added to the beaker, and the release rate of oxygen was calculated as the fraction of the expected increase in oxygen content over time. As shown in FIG. 5D, transfer of oxygen from LOMs was complete in less time using 70 vol % (3.9 seconds; 95% CI, 3.1-6.2 seconds) than 90 vol % LOMs (123 seconds; 95% CI, 112-138 seconds) (P<0.0001, linear regression).

Due to their viscosity, 90 vol % LOMs maintained a less fluid form and mixed slowly with blood, accounting for the slow oxygen transfer.

In Vivo Oxygen Transfer.

For in vivo testing, LOMs were manufactured from DSPC and BRU 100 as described above, and were diluted to contain 50-75 mL oxygen gas per dL suspension.

Figure 6A:
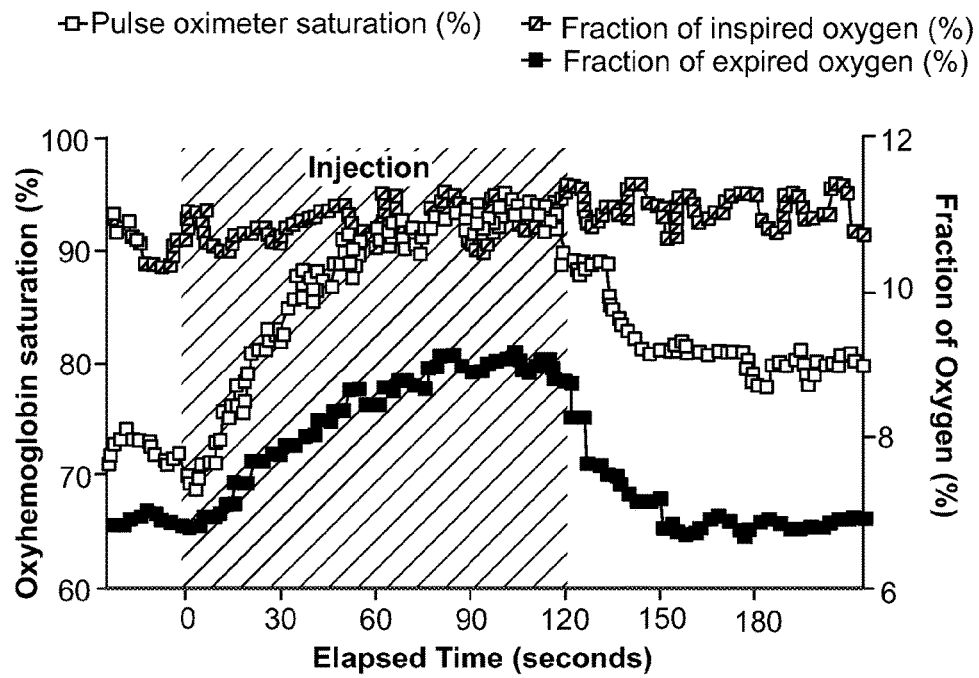
FIG. 6A is a graph showing representative hand injection of LOMs in a hypoxic rabbit from hypoxic ventilation ($FiO_2$ 11%).

In the first model, rabbits (n=10) were anesthetized, intubated and ventilated using 11% oxygen to induce hypoxemia. Oxyhemoglobin saturation was continuously monitored by pulse oximetry. At baseline, oxyhemoglobin saturation was stable near 70%. LOMs were hand injected over 2 minutes, producing a rapid rise in oxygen saturations to >90%, which lasted as long as LOMs were infused (FIG. 6A). Oxygen saturation (middle line) increased rapidly in vivo during the injection of LOMs, and decreased shortly following the end of injection. Contemporaneously, measured oxygen in exhaled gas (bottom line) increased during the injection, consistent with an increase in venous oxygen content. In the cohort of n=10 animals, oxygen saturations were significantly higher by blood gas at 30 (p<0.05), 60, 90 and 120 seconds (p<0.0001) relative to baseline, and the changes became non-significant by 150 seconds. The data shows that shortly after the end of injection, saturations fell to near baseline levels. In addition to raising oxygen saturations, infusions of the LOM formulation also caused an increase in the fraction of oxygen in exhaled gas, consistent with an increase in venous oxygen content.

Figure 6B:
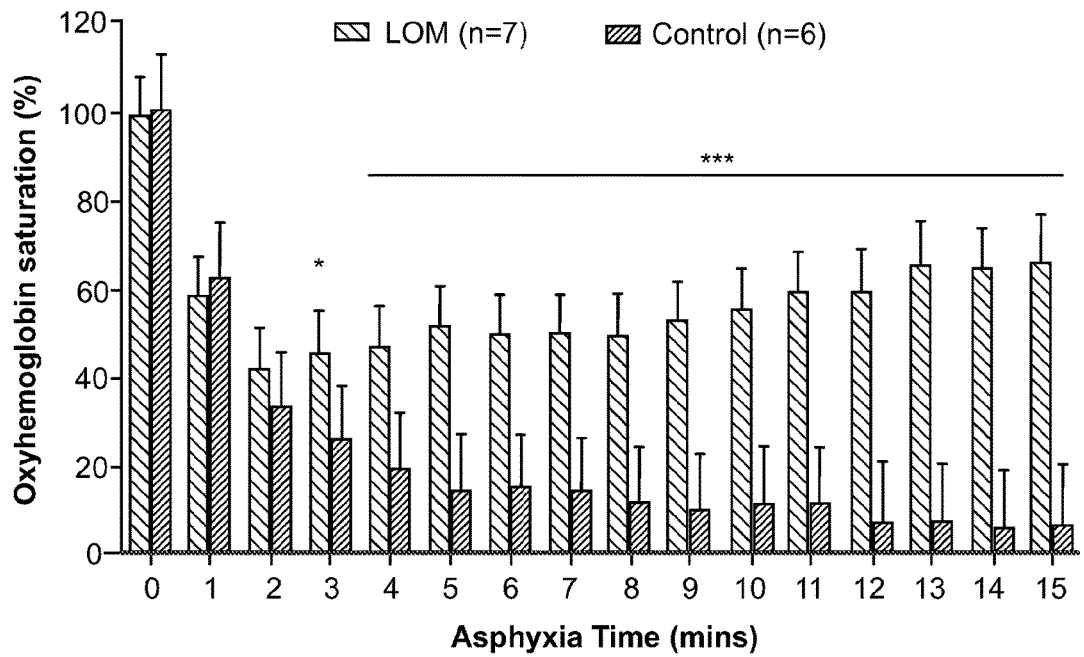
FIG. 6B is a measure of oxyhemoglobin concentration in LOM-treated animals compared to controls. Error bars=95% CI, *, p<0.05, ***, P<0.001.
Figure 6C:
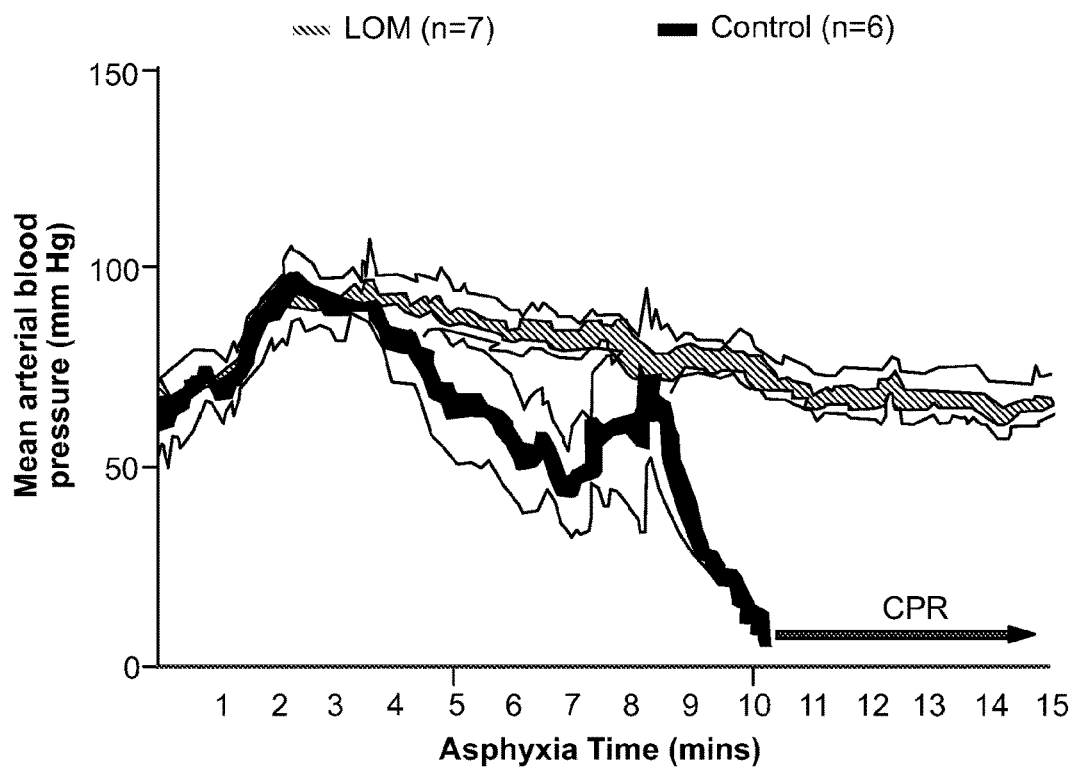
FIG. 6C shows the mean arterial blood pressure as a function of asphyxial time (p=0.002, broken stick model).
Figure 6D:
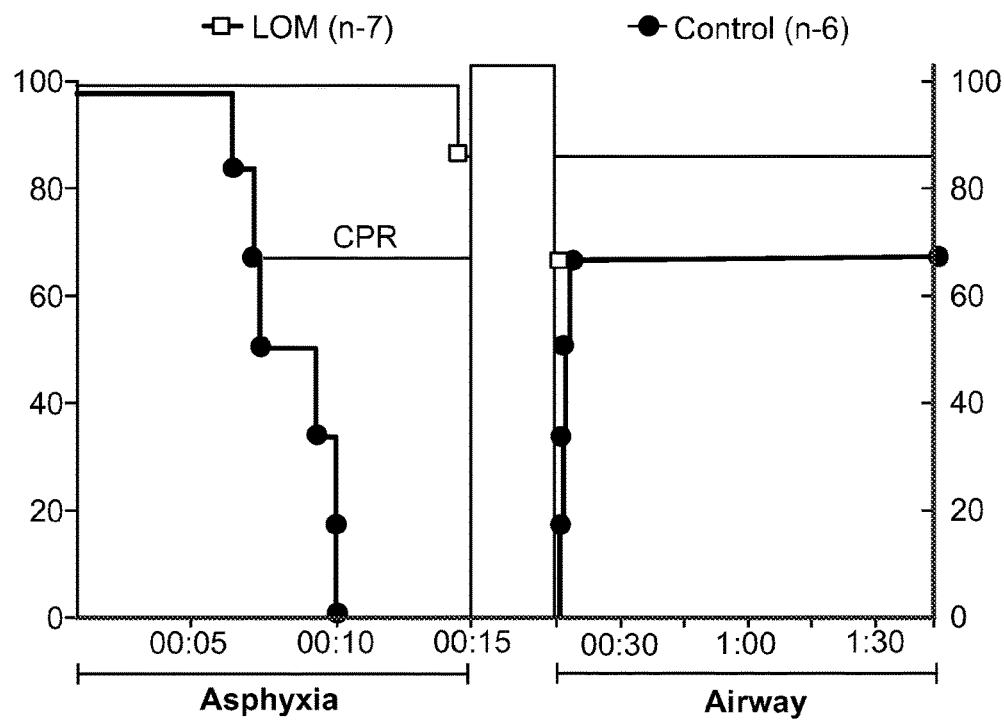
FIG. 6D is a graph showing proportion of animals experiencing cardiac arrest during (left) and following (right) asphyxial period (P=0.0002, log rank test).
Figure 6E:
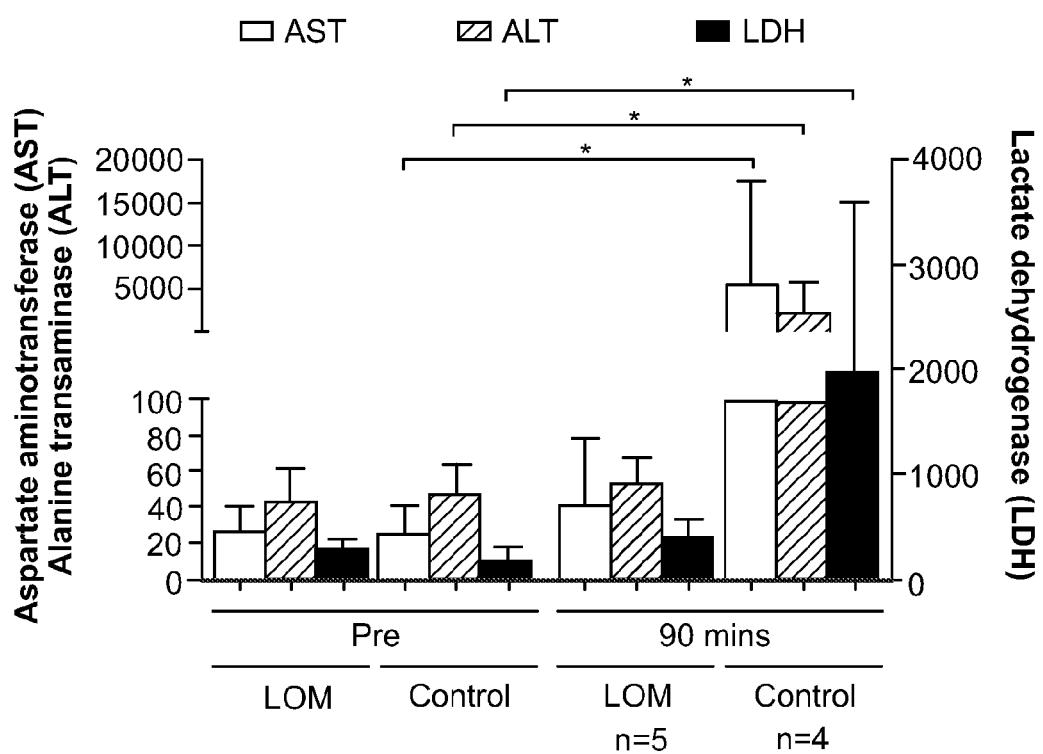
FIG. 6E is a graph showing the effect of LOM administration on liver injury in asphyxiated animals (as measured by Aspartate aminotransferase, alanine transaminase and lactate dehydrogenase levels) when compared to control animals.

In a second experiment, sedated, paralyzed, and intubated rabbits (weight 4-5 kg) were asphyxiated by clamp occlusion of their tracheal tube for 15 minutes and treated with either LOM (n=7) or placebo (n=6) infusion. Animals experiencing a loss of circulation received continuous chest compressions and resuscitative medications but remained asphyxiated for 15 minutes. Surviving animals were supported for 90 minutes prior to sacrifice. Repeated measures were accounted for using a linear mixed effects models with indicator variables at each time point and random intercepts for each animal Results:

Animals treated with LOMs maintained a survivable oxygen saturation and a stable blood pressure (FIGS. 6B and C) throughout asphyxia. They demonstrated a trend towards less metabolic acidosis (p=0.07), increased production of carbon dioxide (p=0.002) and a lower incidence of cardiac arrest relative to controls (p=0.0002, log rank test, FIG. 6D). Hepatic transaminases, markers of liver injury, did not increase in LOM-treated animals but increased significantly at 90 minute survival in control animals. For example, aspartate aminotransferase 90 minutes following asphyxia was 41.20±13.20 in the LOM group, and 5,348±3,881 in the control group (p<0.05). (FIG. 6E). There was no evidence of lung injury in LOM-treated animals, as indicated by markers of oxygen diffusion, dead space ventilation or tissue histology. There was no significant increase in markers of hemolysis in LOM-treated animals. Animals in both groups received comparable volumes of fluid during asphyxia (21.6±3.9 mL fluid/kg LOM-treated, 18.6±3.9 mL/kg control, p=0.222), and did not exhibit differences in central venous pressure.

Example 5: Determination of Lipid-Based Oxygen Microbubble Size Following Intravenous or Intraosseous Injection The size of these particles is important to the safety and efficacy of the suspension following injection. The particles may change in size following the trauma of injection into an intravenous (IV) or intraosseous (IO) line. Studies were conducted to determine change in size distribution of gas filled particles following injection through an IV or an IO line.

Methods:

LOMs are rapidly consumed in living animals. Therefore, a post-mortem model was used to test the effect of infusion on particle sizes. A 4.5 kg rabbit was exsanguinated and the circulatory system flushed with saline A 4 French Cordis sheath was placed into the right femoral vein and a 15 gauge Jamshidi intraosseous needle into the left forelimb. The central veins were dissected out for sampling of LOMs following injection. Eight-20 mL aliquots of LOMs were prepared by admixing a lipid-based solution with oxygen gas under high energy conditions. Particle size distribution of each aliquot was characterized by light scatter (Particle Sizing Systems).

Each aliquot was hand injected into either an IO (n=4) or a central venous line (n=4) at 60 mL/minute. During each infusion, samples of LOM were visualized flowing within veins (LOMs are bright white), and were withdrawn by direct puncture of the vein. The particle size distribution of post-infusion samples was determined by light scatter. Size distributions were compared prior to and following each infusion type by a Mann Whitney test.

Figure 7A:
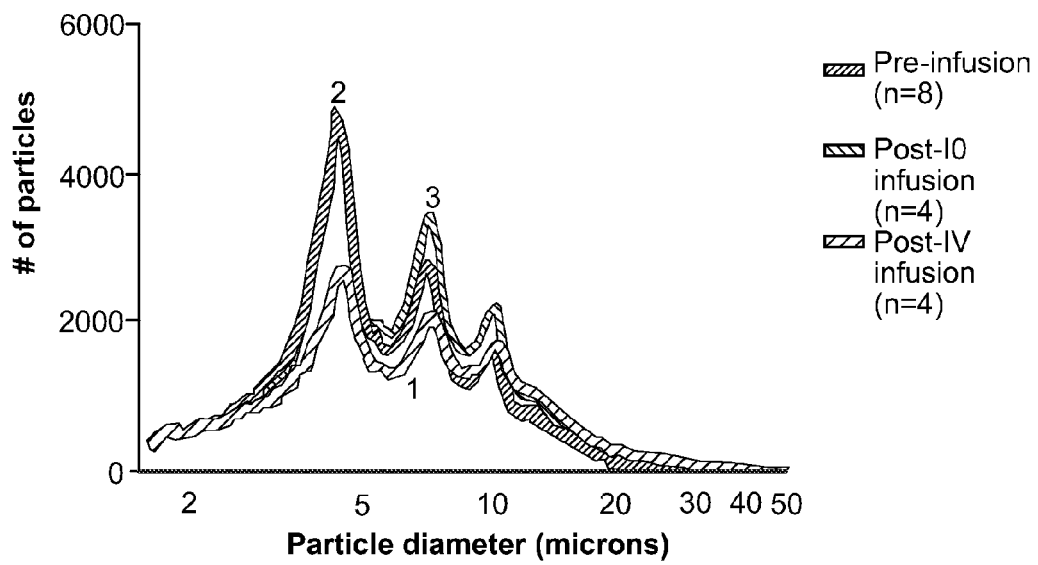
FIG. 7A is a graph showing particle distribution of lipid-based oxygen microbubbles following intravenous (IV) and intraosseous (IO) injection. 1=Post IV infusion; 2=Pre infusion; 3=Post IO infusion.

Results:

Suspensions contained a mean diameter of 6.45±3.08 microns prior to infusion, 7.38±4.84 microns following IV infusion and 6.31±4.28 microns following IO infusion. Compared to pre-infusion sizes, particle size distributions did not differ following either IV ($p=0.8399$) or IO ($p=0.8621$) infusions (FIG. 7).

Conclusion:

In a post-mortem model, LOMs do not change in size following injection through an IV or an IO line.

Example 6: Arterial Oxygen Content Following Continuous Chest Compression CPR

Continuous chest compression only (CCC) CPR may increase bystander response rates for CPR. However, patients receiving prolonged CCC CPR may exhibit alveolar and arterial hypoxia. A study was conducted to measure arterial oxygen content during CCC CPR following a brief period of untreated ventricular fibrillation (VF).

Methods:

Yorkshire swine (n=2, mean 27.9 kg) were anesthetized using Telazol and Xylazine for intubation and mechanical ventilation (pressure control, PIP 15 cm $H_2O$, PEEP 3 cm $H_2O$, $FiO_2$ 21%). Instrumentation included arterial and venous access, as well as an indwelling arterial $PO_2$ probe, and cerebral near infrared resonance spectroscopy (NIRS). Animals were kept spontaneously breathing, and anesthesia was titrated to comfort. Following VF, the ventilator was disconnected and the endotracheal tube removed. Following 6 minutes of untreated ventricular fibrillation, 6 minutes of continuous anteroposterior chest compressions without ventilation were performed by trained providers. Real time feedback was given by a Zoll M series defibrillator. Following defibrillation, continuous chest compressions and resuscitative measures were initiated but animals were not ventilated. Endpoints included arterial blood gases drawn at the end of each phase, measured tidal volumes and continuous $PO_2$ measurements.

Figure 8A:
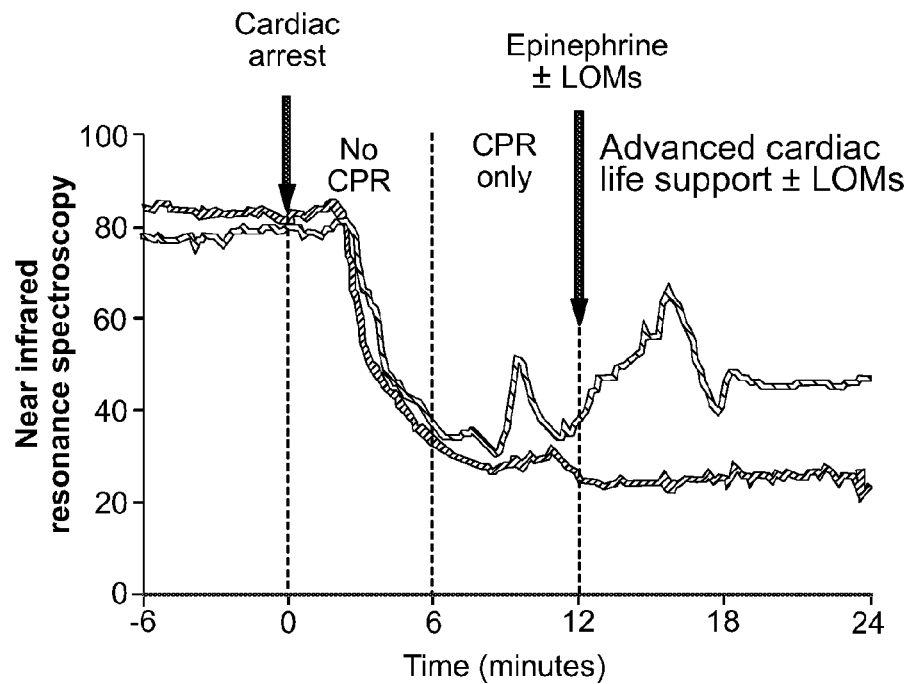
FIG. 8A is a graph depicting the cerebral oxygen response during a swine model of out of hospital cardiac arrest (n=1). The animal was extubated and not ventilated for the entire treatment period and passed through untreated ventricular fibrillation (0-6 minutes), then chest compression only CPR from minutes 6-12 was administered, then the animal was treated with standard of care with or without the addition of bolus LOMs.
Figure 8B:
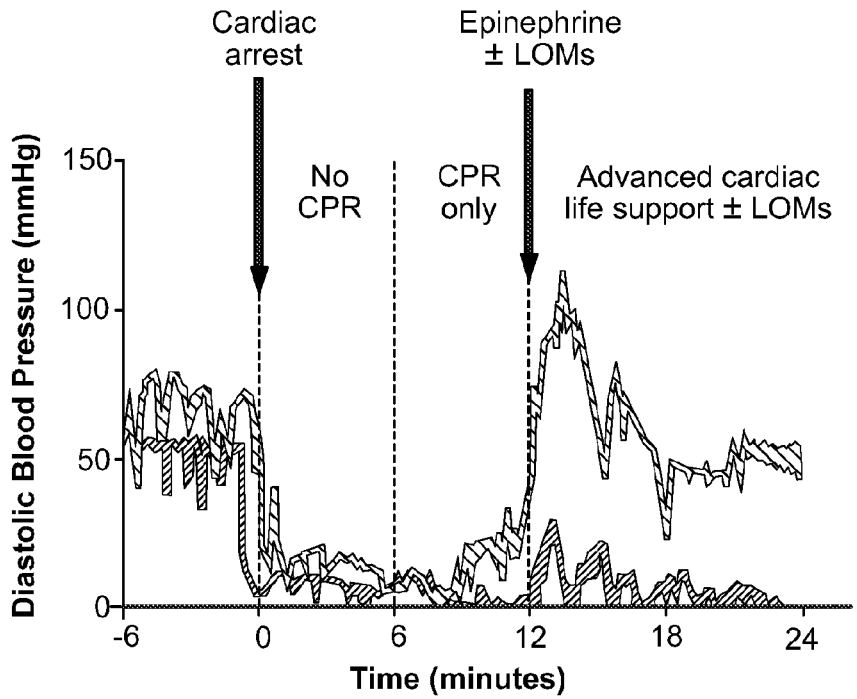
FIG. 8B depicts the diastolic blood pressure response (and therefore, the coronary perfusion pressure) in animals treated as described above for FIG. 8A.

Results:

Chest compressions were in target range (1.5-3 inches depth and rate 100-120/min) 84.9±8.3% of the time. NIRS was normal at baseline, and decreased immediately and profoundly following the onset of VF, increased transiently during initiation of continuous chest compression only (CCC) CPR, and then increased dramatically following intravenous injection of LOMs. By contrast, NIRS did not increase during standard advanced cardiac life support without the use of LOMs (FIG. 8, top).

This suggests that administration of LOMs in bolus form during CPR may improve cerebral oxygen delivery as an adjunct to conventional resuscitative techniques. Further, diastolic blood pressure during the same experiment was seen to increase dramatically further when LOMs were co-administered with the first dose of Epinephrine relative to controls. This may lead to a larger coronary perfusion pressure during CPR and improved resuscitation rates in patients treated with LOMs during cardiac arrest.

Example 7: Administration of Injectable Oxygen Suspension Rapidly Reverses Hypoxemia Via Intravenous or Intraosseous Route Hypoxemia contributes to cellular dysfunction and death in a number of critical illness states. A study was conducted to evaluate the possibility of rapidly reversing severe hypoxemia using intravenous and intraosseous infusions of lipid-based oxygen microparticles (LOMs).

Methods:

LOMs were manufactured from a lipid-based mixture of DSPC and cholesterol combined with oxygen gas using a process of shear homogenization as described above.

LOM diameter was determined by light scatter and oxygen content was determined by weight differential of a set volume of suspension. Adult New Zealand rabbits were anesthetized, paralyzed and mechanically ventilated. Venous, arterial and intraosseous lines were placed in the rabbits. Hypoxemia was induced by ventilation with 10% oxygen. Following observation for 2 minutes, infusions of LOMs were administered at varying rates over a 2 minute period via either intravenous (n=5) or intraosseous line (n=9), followed by a 1 minute observation period. Endpoints included oxyhemoglobin saturations by pulse oximetry and arterial blood gas values drawn every 30 seconds. Endpoints during infusions were compared to baseline by two way ANOVA with Bonferroni post-tests.

Results.

LOM suspensions contained 52.8±3 0 mL of oxygen gas per dL of suspension. Mean particle diameter was 6.42 microns.

Figure 9A:
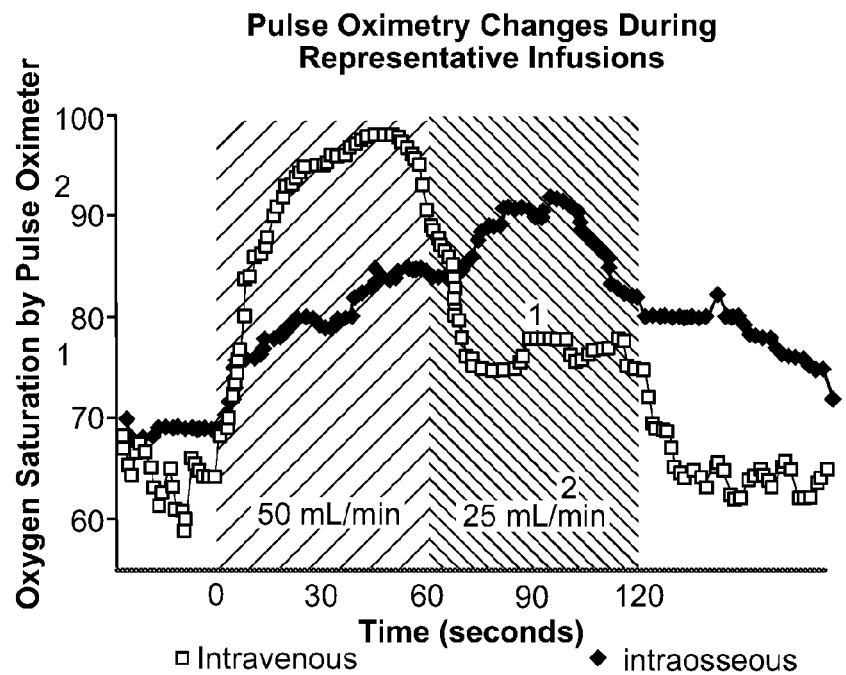
FIG. 9A is a graph depicting oxygen saturation of representative animals following intravenous (1) and intraosseous (2) administration of LOM infusions at 50 mL/min (left half) and at 25 mL/min (right half).
Figure 9B:
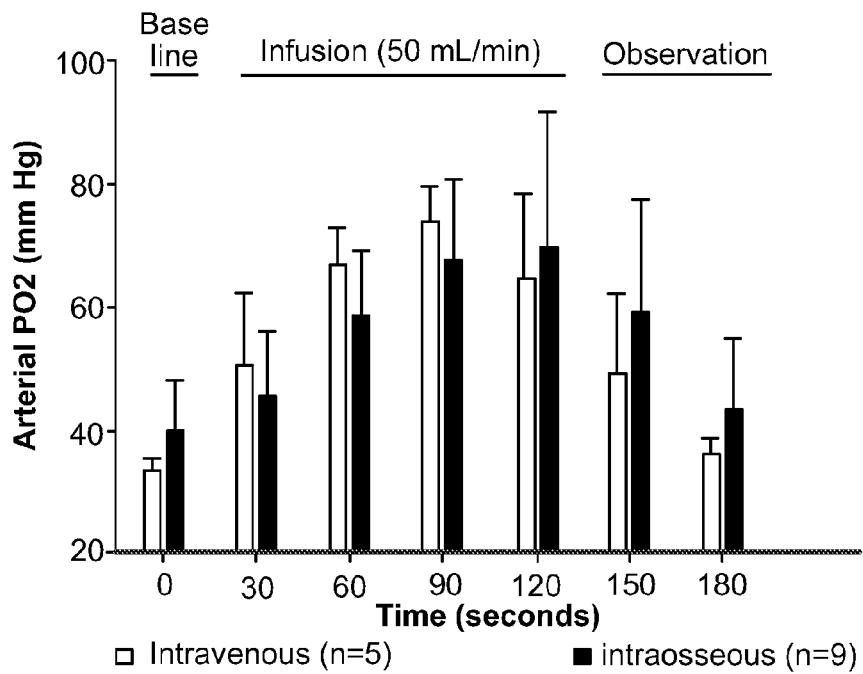
FIG. 9B is a graph showing arterial oxygen tension as a function of time following intravenous (left bar for each bar pair), or intraosseous (right bar for each bar pair) administration of lipid-based oxygen microbubbles.
Figure 9C:
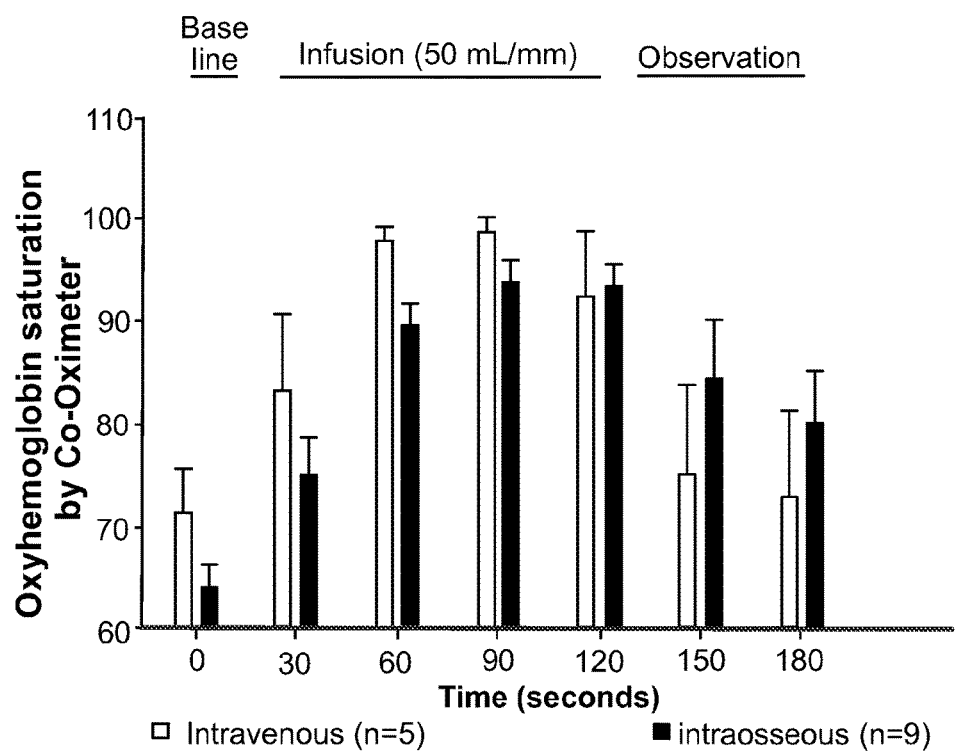
FIG. 9C is a graph showing oxyhemoglobin saturation (as measured by co-oximetry) as a function of time during intravenous (left bar for each bar pair), or intraosseous (right bar for each bar pair) administration of LOMs.

Oxyhemoglobin saturation by pulse oximeter rose rapidly in a dose-dependent fashion in both intravenous and intraosseous infusions (FIG. 9A). Relative to baseline measures, arterial $PO_2$ (FIG. 9B) and oxyhemoglobin saturation by co-oximeter (FIG. 9C) increased during IV and IO infusions ($p<0.0001$ for both groups).

There was a non-significant trend that the increase in oxyhemoglobin saturations was delayed in intraosseous infusions relative to intravenous infusions.

Conclusion:

Oxyhemoglobin saturation and oxygen tension can be acutely raised by intravenous or intraosseous infusion of LOMs.

Example 8: Freezing and Thawing of LOMs

Methods: LOMs were manufactured as described above using Combination C and concentrated to 90 vol % by centrifugation. 30 mL aliquots were placed into 60 mL plastic syringes (Beckton Dickenson) (n=15) and stored at −20° C. for 1 hour. This resulted in a clearly frozen LOM cake.

Figure 7B:
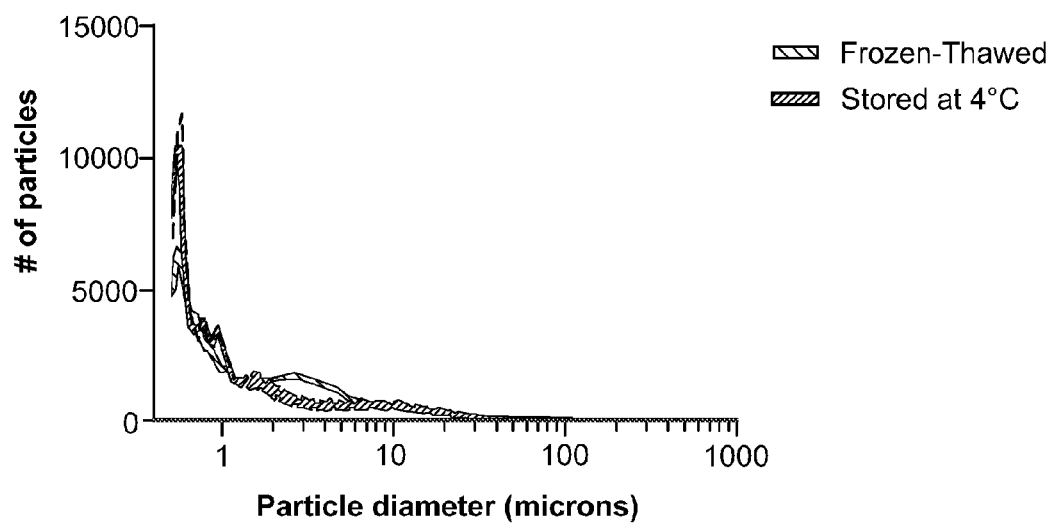
FIG. 7B is a size distribution plot of LOMs composed of Combination C which were stored at 4° C. for 1 week, and that were frozen at −20° C. and subsequently thawed by running under water 42° C. for 30 seconds.

Syringes were then removed and heated using one of three methods (n=5 each): left to stand at room temperature for 1 hour, exposed to 42° C. water for 30 seconds or microwaved at 1100 Watts for 10 seconds. These methods resulted in no product loss and no difference in size distribution (FIG. 7B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for forming a concentrated oxygen-containing lipid-based microbubble suspension comprising:
    (a) forming a precursor mixture comprising a fluid carrier and one or more lipids, and optionally comprising one or more stabilizing agents, and
    (b) subjecting the precursor mixture to high shear homogenization using an inline, closed system homogenizer, wherein the suspension is homogenized at a shear rate ranging from approximately 4000 RPM to approximately 9000 RPM, wherein oxygen gas is fed into the homogenizer at a flow rate ranging from 0.05 L/min to 10 L/min, for a sufficient period of time to produce a lipid-based microbubble suspension comprising at least 50% oxygen by volume and wherein there is no fluorocarbon in the microbubble suspension.

2. The method of claim 1, wherein the suspension is homogenized at a shear rate ranging from about 7000 RPM to about 8000 RPM.

3. The method of claim 1, wherein the one or more stabilizing agents are selected from the group consisting of cholesterol, polyoxyethylenepolyoxypropylene (Poloxamer 188), and Poly(ethylene glycol)-block-poly(propylene glycol)-block-poly(ethylene glycol) (Pluronic F108).

4. The method of claim 3, wherein the stabilizing agent is cholesterol and the lipid is DSPC.

5. The method of claim 1, wherein the microbubble suspension further comprises one or more excipients selected from the group consisting of thinning agents, viscosity lowering agents, and combinations thereof.

6. The method of claim 1, wherein the microbubble suspension comprises at least 70% oxygen by volume.

7. The method of claim 6, wherein step (b) of claim 1 is repeated via one or more passes through the homogenizer until the microbubble suspension contains the oxygen suspension has a sufficient concentration of oxygen, wherein no further processing step is needed to obtain the concentration of oxygen.

8. The method of claim 1, further comprising centrifuging the microbubble suspension to separate a microbubble phase from a liquid phase, wherein the microbubble phase comprises microbubbles having a size of predominantly 10 microns or lower.

9. The method of claim 1, further comprising freezing the microbubble suspension, at a temperature of approximately 0° C., wherein when the suspension is subsequently thawed by exposing to warmed water, convective heat, or a microwave for a period of less than 5 minutes the size distribution and oxygen concentration of the microbubble suspension is the same as it was prior to the freezing step.

10. The method of claim 1, wherein the microbubble suspension comprises at least 80% oxygen by volume.

11. The method of claim 1, wherein the microbubble suspension comprises at least 90% oxygen by volume.

12. The method of claim 1, wherein the microbubble suspension comprises at least 95% oxygen by volume.

13. The method of claim 1, further comprising freezing the microbubble suspension, at a temperature of approximately 0° C., wherein when the suspension is subsequently thawed by exposing to warmed water, convective heat, or a microwave for a period of less than 30 seconds, the size distribution and oxygen concentration of the microbubble suspension is the same as it was prior to the freezing step.

14. The method of claim 1, further comprising centrifuging the microbubble suspension at a force between 300 and 2000 RPM and for a period of at least 5 minutes to separate a microbubble phase from a liquid phase, wherein the microbubble phase comprises microbubbles having a size of predominantly 10 microns or lower.

* * * * *

UNITED STATES PATENT AND TRADEMARK OFFICE
CERTIFICATE OF CORRECTION

PATENT NO. : 10,357,450 B2  
APPLICATION NO. : 14/390665  
DATED : July 23, 2019  
INVENTOR(S) : John Kheir et al.

Page 1 of 1

It is certified that error appears in the above-identified patent and that said Letters Patent is hereby corrected as shown below:

On the Title Page

Item (60): In the section "Related U.S. Application Data", please replace "61/261,261" with – 61/621,261 –

Signed and Sealed this  
Seventh Day of January, 2020

Andrei Iancu  
*Director of the United States Patent and Trademark Office*